(12) United States Patent
Ranjan et al.

(10) Patent No.: US 9,138,411 B2
(45) Date of Patent: Sep. 22, 2015

(54) CURCUMIN-ER, A LIPOSOMAL-PLGA SUSTAINED RELEASE NANOCURCUMIN FOR MINIMIZING QT PROLONGATION FOR CANCER THERAPY

(71) Applicants: University of North Texas Health Science Center, Fort Worth, TX (US); SignPath Pharma Inc., Quakertown, PA (US)

(72) Inventors: Amalendu Prakash Ranjan, Fort Worth, TX (US); Anindita Mukerjee, Fort Worth, TX (US); Jamboor K. Vishwanatha, Fort Worth, TX (US); Lawrence Helson, Quakertown, PA (US)

(73) Assignees: University of North Texas Health Science Center at Fort Worth, Fort Worth, TX (US); SignPath Pharma, Inc., Quakertown, PA (US)

( * ) Notice: Subject to any disclaimer, the term of this patent is extended or adjusted under 35 U.S.C. 154(b) by 0 days.

(21) Appl. No.: 14/016,056

(22) Filed: Aug. 31, 2013

(65) Prior Publication Data

US 2014/0065061 A1 Mar. 6, 2014

Related U.S. Application Data

(60) Provisional application No. 61/695,827, filed on Aug. 31, 2012.

(51) Int. Cl.
| | | |
|---|---|---|
| A61K 9/14 | (2006.01) | |
| A61K 31/12 | (2006.01) | |
| A61K 9/51 | (2006.01) | |
| A61K 45/06 | (2006.01) | |

(52) U.S. Cl.
CPC .............. *A61K 9/145* (2013.01); *A61K 9/141* (2013.01); *A61K 9/5123* (2013.01); *A61K 9/5153* (2013.01); *A61K 31/12* (2013.01); *A61K 45/06* (2013.01)

(58) Field of Classification Search
CPC ...................................................... A61K 9/141
See application file for complete search history.

(56) References Cited

U.S. PATENT DOCUMENTS

| | | | |
|---|---|---|---|
| 4,812,312 A | 3/1989 | Lopez-Berestein et al. | |
| 5,023,087 A | 6/1991 | Yau-Young | |
| 5,679,864 A | 10/1997 | Krackov et al. | |
| 6,143,276 A | 11/2000 | Unger | |
| 7,060,733 B2 | 6/2006 | Pandol et al. | |
| 7,067,159 B2 | 6/2006 | Katz et al. | |
| 7,507,864 B2 | 3/2009 | Miller et al. | |
| 7,674,820 B2 | 3/2010 | Fedida et al. | |
| 7,723,515 B1 | 5/2010 | DiMauro | |
| 7,871,609 B2 | 1/2011 | Ziff et al. | |
| 7,968,115 B2 | 6/2011 | Kurzrock | |
| 8,062,663 B2 | 11/2011 | Wang et al. | |
| 8,153,172 B2 | 4/2012 | Antony | |
| 8,202,839 B1 | 6/2012 | Sung | |
| 8,207,219 B2 | 6/2012 | Fedida et al. | |
| 2001/0051184 A1 | 12/2001 | Heng | |
| 2002/0048598 A1 | 4/2002 | Malik | |
| 2005/0181036 A1 | 8/2005 | Aggarwal et al. | |
| 2005/0233970 A1 | 10/2005 | Garnick | |
| 2005/0266067 A1 | 12/2005 | Sengupta et al. | |
| 2006/0067998 A1 | 3/2006 | Kurzrock et al. | |
| 2006/0147512 A1 | 7/2006 | Sabin | |
| 2007/0048284 A1 | 3/2007 | Donahue et al. | |
| 2008/0075671 A1 | 3/2008 | Di Mauro | |
| 2008/0103213 A1 | 5/2008 | Kurzrock et al. | |
| 2008/0107749 A1 | 5/2008 | Maitra et al. | |
| 2008/0138400 A1 | 6/2008 | Kurzrock et al. | |
| 2008/0253961 A1 | 10/2008 | Braden et al. | |
| 2008/0255464 A1 | 10/2008 | Vincent | |
| 2009/0143433 A1 | 6/2009 | Hendrix | |
| 2009/0246770 A1 | 10/2009 | Levy | |
| 2009/0317387 A1 | 12/2009 | Paton et al. | |
| 2009/0324703 A1 | 12/2009 | Frautschy et al. | |
| 2010/0004549 A1 | 1/2010 | Kohls et al. | |
| 2010/0048957 A1 | 2/2010 | Kim | |
| 2010/0093873 A1 | 4/2010 | Goldfischer | |
| 2010/0151000 A1 | 6/2010 | Thomas et al. | |
| 2010/0179103 A1 | 7/2010 | Desai | |

(Continued)

FOREIGN PATENT DOCUMENTS

| | | | |
|---|---|---|---|
| CA | 2584279 A1 | 4/2005 | |
| JP | H10-191927 A | 7/2010 | |

(Continued)

OTHER PUBLICATIONS

Nam et al, Curcumin-Loaded PLGA Nanoparticles Coating onto Metal Stent by Electrophoretic Deposition Techniques, Bull. Korean Chem. Soc, 2007, 38(3), 397-402.*
Zhang et al, Self-Assembled Lipid-Polymer Hybrid Nanoparticles: A Robust Drug Delivery Platform, ACS Nano, 2008, 2(8), 1696-1702.*
FDA Guidance for Industry regarding s7B Nonclinical Evaluation of the Potential for Delayed Ventricular Repolarization (Qt Interval Prolongation) by Human Pharmaceuticals S7B, Oct. 2005.*
Li et al, Liposome-Encapsulated Curcumin, In Vitro and In Vivo Effects on Proliferation, Apoptosis, Signaling, and Angiogenesis, Cancer, 2005, 104(6), 1322-1331.*
Murphy, Eric, A., et al., "Targeted Nanogels: A Versatile Platform for Drug Delivery to Tumors," Molecular Cancer Therapeutics, Apr. 25, 2011; 10:972-982.
International Search Report and Written Opinion for PCT/US2013/057744 dated Dec. 12, 2013.

(Continued)

*Primary Examiner* — Paul Dickinson
(74) *Attorney, Agent, or Firm* — Edwin S. Flores; Chalker Flores, LLP

(57) ABSTRACT

The present invention includes compositions and methods of making a nanoparticle composition comprising a polymeric core comprising one or more polymers and one or more active agents, and at least one layer of one or more lipids on the surface of the polymeric core; more specifically, the invention relates to the use of curcumin within such a lipid-polymer nanoparticle formulation for minimizing QT prolongation associated with curcumin in treatment of cancer.

14 Claims, 17 Drawing Sheets

(56) References Cited

U.S. PATENT DOCUMENTS

| | | |
|---|---|---|
| 2010/0239552 A1 | 9/2010 | Mayoux et al. |
| 2010/0240581 A1 | 9/2010 | Tortoriello et al. |
| 2011/0117186 A1 | 5/2011 | Helson |
| 2011/0229555 A1 | 9/2011 | Helson et al. |
| 2011/0287085 A1 | 11/2011 | Kurzrock et al. |
| 2012/0003177 A1 | 1/2012 | Shen |
| 2012/0021036 A1 | 1/2012 | Majeti et al. |
| 2012/0058208 A1 | 3/2012 | Jacob |
| 2012/0237590 A1 | 9/2012 | Helson |
| 2012/0308643 A1 | 12/2012 | Helson |
| 2013/0310351 A1 | 11/2013 | Milan et al. |
| 2013/0337488 A1 | 12/2013 | Helson |

FOREIGN PATENT DOCUMENTS

| | | |
|---|---|---|
| WO | 0070949 A1 | 11/2000 |
| WO | 2004047717 A2 | 6/2004 |
| WO | 2004080396 A2 | 9/2004 |
| WO | 2006061101 A2 | 6/2006 |
| WO | 200706028 A2 | 5/2007 |
| WO | 2007103435 A2 | 9/2007 |
| WO | 2008045534 A2 | 4/2008 |
| WO | 2008063513 A2 | 5/2008 |
| WO | 2008128123 A2 | 10/2008 |
| WO | 2009051837 A2 | 4/2009 |
| WO | 2010009186 A1 | 1/2010 |
| WO | 2010033692 A1 | 3/2010 |
| WO | 2010057332 | 5/2010 |
| WO | 2011063178 A2 | 5/2011 |
| WO | 2011001351 | 6/2011 |
| WO | 2011119588 A1 | 9/2011 |
| WO | 2012125830 A2 | 9/2012 |
| WO | 2012167212 A2 | 12/2012 |
| WO | 2013188767 A1 | 12/2013 |

OTHER PUBLICATIONS

Fauchier, L., et al.,"JP: Effect of Verapamil on QT Interval Dynamicity," AM J Cardiol., 1999; 83(5):807-808 A10-1.

Fowler, NO, et al., "Electrocardiographic Changes and Cardiac Arrhythmias in Patients Receiving Psychotropic Drugs," Am J Cardiol, 1976; 37(2):223-230.

Garcia-Alloza, M., et al., "Curcumin Labels Amyloid Pathology in Vivo, Disrupts Existing Plaques, and Partially Restroes distorterneurites in an Alzheimer Mouse Model," Journal of Neurochemistry, (2007), vol. 102, pp. 1095-1104.

Grama, C.N., et al., "Poly(lactide-glycolide) nanoparticles for peroral delivery of bioactives," Current Opinion in Colloid and Interface Science, London, GB, vol. 16, No. 3, Nov. 24, 2010, pp. 238-245.

Gukovsky, Ilya, et al., "Curcumin Ameliorates Ethanol and Nonethanol Experimental Pancreatitis," Am. J. Physiol. Gastrointest. Liver Physiol., (2003), 284:G85-G95.

Hernandez-Fonseca , Juan P., et al., "Structural and Ultrastructural Analysis of Cerebral Cortex, Cerebellum, and Hypothalamus from Diabetic Rats," Experimental Diabetes Research Oct. 1, 2009: 329632.

Jacob, Asha, et al., "Mechanism of the Anti-Inflammatory Effect of Curcumin: PPAR-y Activation," Hindawi Publishing Corporation, PPAR Research, (2007), Article ID 89369, 5 pages.

Jervell, A, et al., "Congenital Deaf-Mutism, Functional Heart Disease with Prolongation of the QT Interval and Sudden Death," Am Heart J., 1957; 54(1):59-68.

Kang, J, et al., "Discovery of a Small Molecule Activator of the Human Ether-a-go-go—Related Gene(HERG) Cardiac K+ Channel," Mol Pharmacol, 2005(3); 67:827-836.

Katchman, AN, et al., "Comparative Evaluation of HERG Currents and QT Intervals Following Challenge with Suspected Torsadogenic and Nontorsdogenic Drugs," J Pharmacol Exp Ther., 2006; 316(3):1098-1106.

Kessler, Ronald C., et al., "Posttraumatic Stress Disorder in the national Comorbidity Survey," Archives of General Psychiatry, vol. 52, No. 12, pp. 1049-1060.

Kim, So Jung, et al., "Curumin Stimulates Proliferation of Embryonic Neural Progenitor Cells and Neurogenesis in the Adult Hippocampus," The Journal of Biological Chemistry, May 23, 2008, vol. 283, No. 21, pp. 14497-14505.

Koehler, Jacqueline A., et al., "Glucagon-Like Peptide-1 Receptor Activation Modulates Pancreatitis-Associated Gene Expression Bud Does Not Modify the Susceptibility to Experimental Pancreatitis in Mice," Diabetes, Sep. 2009, vol. 58, pp. 2148-2161.

Konwarh, R., et al., "Poly(ethylene glycol)-magnetic nanoparticles-curcumin trio: Directed morphogenesis and synergistic free-radical scavenging," Colloids and Surfaces B: Biointerfaces, vol. 81, Aug. 7, 2010, pp. 578-586.

Kourelis, Taxiarchis V., et al., "Metformin and Cancer: New Applications for an Old Drug," Med. Oncol., Feb. 8, 2011, 14 pages.

Kowluru, Renu A., et al., "Effects of Curcumin on Retinal Oxidative Stress and Inflammation in Diabetes," Nutrition & Metabolism, Apr. 16, 2007, 8 pages.

Kulkarni, S.K., et al., "An Overview of Curcumin in Neurological Disorders," Indian J. Pharm. Sci, Jul. 1, 2010, 72:2, pp. 149-154.

Kumar, T. Peeyush, et al., "Curcumin Modulates Dopaminergic Receptor, CREB and Phospholipase C Gene Expression in the Cerebral Cortex and Cerebellum of Streptozotocin Induced Diabetic Rats," Journal of Biomedical Science, (2010), 2:43, 11 pages.

Lamont, Benjamin J., et al., "Differential Antidiabetic Efficacy of Incretin Agonists Versus DPP-4 Inhibition in High Fat-Fed Mice," Diabetes, Jan. 2008, vol. 57, pp. 190-198.

Li, Yu-Cheng, et al., "Antidepressant-Like Effects of Curcumin on Serotonergic Receptor-Coupled Ac-cAMP Pathway in Chronic Unpredictable Mild Stress of Rats," Progress in Neuro-Psychophamacoloby & Biological Psychiatry, (2009), vol. 33, pp. 435-449.

Li, Lan, et al., "Liposome-Encapsulated Curcumin In Vitro and In Vivo Effects on Proliferation, Apoptosis, Signaling, and Angiogenesis," Cancer, 104:1322-1331.

Lim, Kah Jing, et al., "A Polymeric Nanoparticle Formulation of Curcumin Inhibits Growth, Clonogenicity and Stem-Like Fraction in Malignant Brain Tumors," Cancer Biology & Therapy, Mar. 1, 2011, 11:5, pp. 464-473.

Logan-Smith, Melanie J., et al., "Curcumin, a Molecule that Inhibits the Ca2+-ATPase of Sarcoplasmic Reticulum but Increases the Rate of Accumulation of Ca2+," The Journal of Biological Chemistry, (2001), vol. 276, No. 50, pp. 46905-46911.

Mach, Claire M., et al., "Determination of Minimum Effective Dose and Optimal Dosing Schedule for Liposomal Curcumin in a Xenograft Human Pancreatic Cancer Model," (2009), Anticancer Research, 29:1895-1900.

Maciel, NR, et al., "Reduced Cardiovascular Alterations of Tarter Emetic Administered in Long-Circulating Liposomes in Rats," Toxicology Letters, 2010; 199(3):234-238.

Marino, Silvia, et al., "Sertaline in the Treatment of Depressive Disorders in Patients with Parkinson's Disease," Neurological Sciences, Nov. 2008, 29:391-395.

Matsushita, Yuichi, et al., "Activation of Peroxisome Proliferator-Activated Receptor d Inhibits Streptozotocin-Induced Diabetic Nephropathy Through Anti-Inflammatory Mechanisms in Mice," Diabetes, Mar. 2011, vol. 60, pp. 960-968.

Mayer, Lawrence D., et al., "Intravenous Pretreatment with Empty pH Liposomes Alters the Pharmacokinetics and Toxicity of Doxorubicin through In Vivo Active Drug Encapsulation," Journal of Pharmaceutical Sciences, vol. 88, No. 1, Nov. 25, 1998, pp. 96-102.

Mishra, S., et al., "The effect of curcumin (turmeric) on Alzheimer's disease: An overview," Annals of Indian Academy of Neurology, vol. 11:1, 2008, pp. 13-19.

Mukerjee, Anindita, et al., "Formulation, Characterization and Evaluation of Curcumin-Loaded PLGA Nanospheres for Cancer Therapy," (2009), Anticancer Research 29:3867-3876.

Nam, et al., "Curcumin-Loaded PLGA Nanoparticles Coating onto Metal Stent by Electrophoretic Deposition Techniques," Bull. Korean Chem. Soc., Jan. 2007, vol. 28, No. 3, pp. 397-402.

Narala, Venkata R., et al., "Curcumin is not a Ligand for Peroxisome Proliferator-Activated Receptor-Y," Gene Therm. Mol. Biol., Apr. 1, 2009, 13(1):20-25.

(56) References Cited

OTHER PUBLICATIONS

Nousiainen, T., et al., "QT dispersion and late potentials during doxorubicin therapy for non-Hodgkin's lymphoma," Journal of Internal Medicine, 245, 1999, pp. 359-364.
Olansky, Leann, "Do Incretin-Based Therapies Cause Acute Pancreatitis?" Journal of Diabetes Science and Technology, Jan. 2010, vol. 4, Issue 1, pp. 228-229.
Pitman, Roger K., et al., "Conceptually Driven Pharmacologic Approaches to Acute Trauma," CNS Spectrums, Feb. 2005, vol. 10, No. 2, pp. 99-106.
Rajeswari, A., et al., "Inhibition of monoamine oxidase-B by the polyphenolic compound, curcumin and its metabolite tetrahydrocurcumin, in a model of Parkinson's disease induced by MPTP neurodegeneration in mice," Inflammopharmacology, vol. 16, 2008, pp. 96-99.
Roberts, A.N., et al., "Molecular and Functional Characterization of Amylin, a Peptide Associated with Type 2 Diabetes Mellitus," Proc. Natl. Acad. Sci. USA, Dec. 1989, vol. 86, pp. 9662-9666.
Rosi, S., et al., "Chemokine Receptor 5 Antagonist d-Ala-Peptide T-Amide Reduces Microglia and Astrocyte Activation Within the Hippocampus in a Neuroinflammatory Rat Model of Alzheimer's Disease," Neuroscience, (2005), vol. 134, pp. 671-676.
Rui, Pan, et al., "Curcumin Improves Learning and Memory Ability and its Neuroprotective Mechanism in Mice," Chin. Med. J., (2008), vol. 121, No. 9, pp. 832-839.
Rusinek, Henry, et al., "Hippocampal Blood Flow in Normal Aging Measured with Arterial Spin Lavelin at 3T," Magnetic Resonance in Medicine, (2011), 65:128-137.
Schena, Francesco P., et al., "Pathogenetic Mechanisms of Diabetic Nephropathy," J. Am. Soc. Nephrol., (2005), 16:S30-S33.
Segman, RH., et al., "Association Between the Dopamine Transporter Gene and Posttraumatic Stress Disorder," Molecular Psychiatry, (2002), vol. 7, pp. 903-907.
Segman, RH., et al., "Peripheral Blood Mononuclear Cell Gene Expression Profiles Identify Emergent Post-Traumatic Stress Disorder Among Trauma Survivors," Molecular Psychiatry, (2005), vol. 10, pp. 500-513.
Shaikh, J., et al, "Nanoparticle encapsulation improves oral bioavailability of curcumin by at least 9-fold when compared to curcumin administered with piperine as absorption enhancer," European Journal of Pharmaceutical Sciences, Elsevier, Amsterdam, NL, vol. 37, No. 3-4, Jun. 28, 2009, pp. 223-230.
Shimizu, Wataru, et al. "Effects of a K+ Channel Opener to Reduce Transmural Dispersion of Repolarization and Prevent Torsade de Pointes in LQT1, LQT2, and LQT3 Models of the Long-QT Syndrome," Circulation, 2000, 102:706-712.
Singh, Sonal, et al., "Long-Term Risk of Cardovascular Events with Rosiglitazone," JAMA, Sep. 12, 2007, vol. 298, No. 10, pp. 1189-1195.
Smith, Judith A., et al., "Abstract A29: Development of Liiposomal Curcumin as a New Potential Anticancer Agent," Molecular Cancer Therapeutics, Dec. 2009, vol. 8, Issue 12, Supplement 1, 1 page.
Stein, Murray B., et al., "Genetic and Environmental Influences on Trauma Exposure and Posttraumatic Stress Disorder Symptoms: A Twin Study," Am. J. Psychiatry, Oct. 2002, vol. 159, No. 10, pp. 1675-1681.
Sun, M., et al., "Enhancement of transport of curcumin to brain in mice by poly(n-butylcyanoacrylate) nanoparticle," J. Nanopart Res., vol. 12, 2010, pp. 3111-3122.
Tonnesen, Hanne, H., et al, "Studies on curcumin and curcuminoids: XXV. Inhibition of primaquine-induced lysis of human red blood cells by curcumin," International Journal of Pharmaceutics 110 (1994) 161-167.
U.S. Department of Health and Human Services, "Guidance for Industry, S7B Nonclinical Evaluation of the Potential for Delayed Ventricular Repolarization (QT Interval Prolongation) by Human Pharmaceuticals," Oct. 2015, pp. 1-13.
Verma, Richa, et al., "Structural and functional changes in a syntheitic S5 segment of KvLQT1 channel as a result of a conserved amino acid substitution that occurs in LQT1 syndrome of human," Biochimica et Biophysica Acta, 1798, Jan. 2010, pp. 461-470.
Vidal, Alessandra Teixeira, et al., "Prolonged cardioprotective effect of pyridostigmine encapsulated in liposomes," Life Sciences, vol. 86, 2010, pp. 17-23.
Wang, Timothy C., et al., "Pancreatic Gastrin Stimulates Islet Differentiation of Transforming Growth Factor a-Induced Ductular Precursor Cells," The Journal of Clinical Investigation, Inc., Sep. 1993, vol. 92, pp. 1349-1356.
Wesley, Umadevi V., et al., "Role for Dipeptidyl Peptidase IV in Tumor Suppression of Human Non Small Cell Lung Carcinoma Cells," Int. J. Cancer, (2004), 109:855-866.
Wesley, Umadevi V., et al., "Dipeptidyl Peptidase Inhibits Malignant Phenotype of Prostate Cancer Cells by Blocking Basic Fibroblast Growth Factor Signaling Pathway," Cancer Res., (2005), a65:1325-1334.
Wu, Aiguo, et al., "Brain and Spinal Cord Interaction: A Dietary Curcumin Derivative Counteracts Locomotor and Cognitive Deficits After Brain Trauma," Neurohabil Neural Repair, May 2011, 25(4):332-342.
Xu, Ying, et al., "Curcumin Reverses Impaired Hippocampal Neurogenesis and Increases Serotonin Receptor 1A mRNA and Brain-Derived Neurotrophic Factor Expression in Chronically Stressed Rats," Brain Research, (2007), 1162, pp. 9-18.
Zhang, et al., Self-Assembled Lipid—Polymer Hybrid Nanoparticles: A Robust Drug Delivery Platform.
Leung, et al., "Effective stablization of curcumin by association to plasma proteins: human serum albumin and fibronogen," Langmuir, 2009, vol. 25, Issue 10, pp. 5773-5777.
Stansfeld, Phillip, J., et al., "Drug Block of the hERG Potassium Channel: Insight From Modeling," Proteins: Structure, Function and Bioinformatics, Apr. 19, 2007, 68:568-580.
Quan, Xiao-Qing, et al., "Increasing Gap Junction Coupling Reduces Transmural Dispersion of Repolarization and Prevents Torsade de Pointes in Rabbit LQT3 Model," J. Cardiovasc. Electrophysiol., vol. 18, Nov. 2007, pp. 1184-1189.
Extended European Search Report and Europeean Search Opinion for EPO 10832224.9 dated Feb. 26, 2013, 5 pages.
Extended and Supplemental European Search Report for EPO 11760055.1 dated Jun. 13, 2014, 7 pages.
Extended European Search Report and Europeean Search Opinion for EPO 12757689.0 dated Oct. 22, 2014, 7 pages.
Extended European Search Report and European Search Opinion for 12792560.0 dated Oct. 30, 2014, 11 pages.
International Search Report and Written Opinion for PCT/US2010/057332, dated Aug. 2, 2011, 12 pages.
International Search Report and Written Opinion for PCT/US2011/029393, dated Jun. 23, 2011, 17 pages.
International Search Report and Written Opinion for PCT/US2012/029230, dated Sep. 21, 2012, 14 pages.
International Search Report and Written Opinion for PCT/US2012/040637, dated Dec. 12, 2012, 13 pages.
International Search Report and Written Opinion for PCT/US2013/045898, dated Sep. 6, 2013, 12 pages.
Abel, Ted., et al., "Epigenetic Targets of HDAC Inhibition in Neurodegenerative and Psychiatric Disorders," Current Opinion in Pharmacology, (2008), vol. 8, pp. 57-64.
Aggarwal, et al., "The Molecular Targets and Therapeutic Uses of Curcumin in Health and Disease," (2006), Springer, 515 pages.
Anderson, P., et al., "The Hippocampus Book," Oxford University Press, 2006, 102 pages.
Arbiser, Jack L., et al., "Curcumin is an In Vivo Inhibitor of Angiogenesis," Moledular Medicine, (1998), 4:376-383.
Ataie, Amin, et al., "Neuroprotective Effects of the Polyphenolic Antioxidant Agnet, Curcumin, Against Homocysteine-Induced Cognitive Impairment and Oxidative Stress in the Rat," Pharmacology, Biochemistry and Behavior, (2010), vol. 96, pp. 378-385.
Bala, Kiran, et al., "Neuroprotective and Anti-Aging Effects of Curcumin in Aged Rat Brain Regions," Biogerontology, (2006), vol. 7, pp. 81-89.
Begun, A.N., et al., "Curcumin Structure-Function, Bioavailibility, and Efficacy in Models of Neuroinflammation and Alzheimer's Disease," The Journal of Pharmacoloby and Experimental Therapeutics, vol. 326:1, Apr. 15, 2008, pp. 196-208.

(56) References Cited

OTHER PUBLICATIONS

Bentzen, Peter J., et al., "Curcumin Induced Suicidal Erythrocyte Death," Cellular Physiology and Biochemistry, (2007), 19:153-164.
Bisht, Savita, et al., "Polymeric Nanoparticle-Encapsulated Curcumin ("Nanocurcumin"): A Novel Strategy for Human Cancer Therapy," Journal of Nanobiotechnology, (2007), 18 pages.
Bisht, Savita, et al., "Systemic Administration of Polymeric Nanoparticle-Encapsulated Curcumin (NanoCurcTM) Blocks Tumor Growth and Metastases in Preclinical Models of Pancreatic Cancer," Mol. Cancer Ther., (Aug. 2010), 9(8):2255-2264.
Blomgren, Kerstin, et al., "Obesity and Treatment of Diabetes with Glyburide may Both be Risk Factors for Acute Pancreatitis," Diabetes Care, (2002), 25:298-302.
Brownlee, Michael, "Biochemistry and Molecular Cell Biology of Diabetic Complications," Nature, Dec. 13, 2001, vol. 414, pp. 813-820.
Chao, Chun C., et al., "Glia: The Not So Innocent Bystanders," Journal of NeuroVirology, (1996), 2:234-239.
Chen, Shali, et al., "High glucose-induced, endothelin-dependent fibronectin synthesis is mediated via NF-kB and AP-1," Am J. Physiol. Cell Physiol., Sep. 18, 2002, 284:C263-C272.
Chen, et al., "An in vitro study of liposomal curcumin: stability, toxicity and biological activity in human lymphocytes and epstein-barr virus-transformed human B-cells," International Journal of Pharmaceutics, Jan. 2009, vol. 366, Issue 1-2, pp. 133-139.
Chiu, Jane, et al., "Curcumin Prevents Diabetes-Associated Abnormalities in the Kidneys by Inhibiting p300 and Nuclear Factor-kB," Nutrition, (2009), 25:964-972.
Compton, SJ, et al., "Genetically Defined Therapy of Inherited Long-QT Syndrome. Correction of Abnormal Repolarization by Potassium," Circulation, 1996; 94:1018-1022.
Crack, Peter J., et al., "Glutathione Peroxidase-1 Contributes to the Neuroprotection Seen in the Superoxide Dismutase-1 Transgenic Mouse in Response to Ischemia/Reperfusion Injury," Journal of Cerebral Blood Flow and Metabolism, (2003), vol. 23, No. 1, pp. 19-22.
D'Amico, Michele, et al., "Long-Term Inhibition of Dipeptidyl Peptidase-4 in Alzheimer's Prone Mice," Experimental Gerontology 45,3, (2010), 24 pages.
Djeddi, D, et al., "A: Effect of Domperidone on QT Interval in Neonates," J Pediatrics, 2008; 153(5):596-598.
Ducroq, J, et al., "Printemps R, Le Grand M.: Additive Effects Ziprasidone and D,L-Sotalol on the Action Potential in Rabbit Purkinje Fibers and on the hERG Potassium Current," J.Pharmacol. Toxicol Methods, 2005; 52:115-122.
Etheridge, SP, et al., "A New Oral Therapy for Long QT Syndrome: Long Term Oral Potassium Improves Repolarization in Patients with hERG Mutations," J AM Coll Cardiol, 2003; 42:1777-1782.
Everett, Peter C., et al., "Preclinical Assessment of Curcumin as a Potential Therapy for B-CLL," American Journal of Hematology, (2006), 8 pages.
Fahn, Stanlex, "Medical Treatment of Parkinson's Disease," Journal of Neurology, 1998, 245 (Supplement 3): P15-P24.
Anderson, Corey, et al., "Most LQT2 Mutations Reduce Kv11.1 (hERG) Current by a Class 2 (Trafficking-Deficient) Mechanism," Circuilation, Nov. 11, 2005, pp. 365-373.
Crouch, et al., "Clinical Relevance and Management of Drug-Related QT Interval Prolongation," Pharmacotherapy, Nov. 7, 2003, vol. 23:7, pp. 881-908.
Doherty, K., et al., "Multi-parameter in vitro toxicity testing of crizotinib, sunitinib, erlotinib, and nilotinib in human cardiomyocytes," Toxicoloty and Applied Pharmacology, Apr. 28, 2003, vol. 272, pp. 245-255.
FDA Pharmacology Review of Xalkori (crizotinib), IND No. 202570, 2011a, www.accessdata.fda.gov/drugsatfda_docs/nda/2011/202570Orig1s000PharmR.pdf (accessed Oct. 9, 2013).
FDA Pharmacology of Tasigna® (nilotinib), IND No. 22-068, 2007a, www.accessdata.fda.gov/drugsatfda_docs/nda/2007/022068s000_PharmR_P1.pdf and www.accessdata.fda.gov/drugsatfda_docs/nda/2007/022068s000_MedR_P2.pdf, (accessed Oct. 25, 2013).
Helson, et al., "Infusion pharmacokinetics of lipocure (liposomal curcumin) and its metabolite tetrahydrocurcumin in beagle dogs," Anticancer Research, Oct. 2012, vol. 32, No. 10, pp. 4365-4370.
Helson, et al., "Liposome mitigation of curcumin inhibition of cardiac potassium delayed-rectifier current," Journal of Receptor, Ligand and Channel Research, Nov. 15, 2012, vol. 5, pp. 108.
International Search Report and Written Opinion for PCT/US2014/071246, dated Mar. 27, 2015, 14 pages.
Kim, K-P., et al., "Nilotinib in Patients with GIST who failed imatinib and sunitinib: importance of prior surgery on drug bioavailability," Jul. 12, 2010, Cancer Chemother. Pharmacol., vol. 68, pp. 285-291.
Layton, D, et al., "Prolongation of the QT interval and cardiac arrhythmias associated with cisapride: limitations of the pharmacoepidemiological studies conducted and proposals for the future," Pharmacoepidemiol Drug Saf., 12(1), Nov. 13, 2002, pp. 31-40.
Lee, et al., "Electrophysiological Effects of the Anti-Cancer Drug Lapatinib on Cardiac Repolarization," Basic & Clinical Pharmocology & Toxicology, vol. 107, Dec. 21, 2009, pp. 614-618.
Mehta, RT, et al., "Formulation, toxicity, and antifungal activity in vitro of liposomal-encapsulated nystatin as therapeutic agent for systemic candidiasis," Antimicrob Agents Chemother., 31(12), Dec. 1987, pp. 1897-1900.
Moha, H, et al., "Curcumin blocks the recombinant human cardiac KCNQ 1/KCNE 1 channels (IKs) stably expressed in HEK 293 cells," Abstract of 12th Annual Meeting of the French Society of Pharmacology and Therapeutics, Fund. & Clin. Pharma., vol. 22:1, Jun. 2008.
Mosse, et al., "Safety and activity of crizotinib for pediatric patients with refractory solid tumours of anaplastic large-cell lymphoma: a Children's Oncology Group phase 1 consortium study," Lancet Oncol., May 2013, vol. 14(6), pp. 472-480.
Naseem, et al., "Bupivacaine Extended Release Lispome Injection Does not Prolong Qtc Interval in a Thorough QT/QTc Study in Healthy Volunteers," Journal of Clin. Pharma., 2012, vol. 52, pp. 1441-1447.
Shah, et al., "Cardiovascular Safety of Tyrosine Kinase Inhibitors: With a Special Focus on Cardiac Repolarisation (QT Interval)," Drug Saf., Apr. 26, 2013, vol. 36, pp. 295-316.
Shimizu, Wataru, et al., "Sodium Channel Block with Mexiletine is Effective in Reducing Dispersion of Repolarization and Preventing Torsade de Pointes in LQT2 and LQT3 Models of the Long-QT Syndrome," vol. 96, Apr. 28, 1997, pp. 2038-2047.
Tasigna Package insert, Novartis Pharmaceuticals, Revised Sep. 2013.
Van De Water, et al., "An Improved Method to Correct the QT Interval of the Electrocardiogram for Changes in Heart Rate," Journal of Pharmacological Methods, Apr. 1989, vol. 22, pp. 207-217.
Witchel, "Drug-induced hERG Block and Long QT Syndrome," Cardiovascular Therapeutics, 2011, vol. 29, pp. 251-259.
Yap, Y. G., et al., "Drug Induced QT Prolongation and Torsades de Pointes," Heart, vol. 89, Nov. 2003, pp. 1363-1372.
Zachariae, U., et al., "Side chain flexabilities in the human ether-a-go-go related potassium channel (hERG) together with matched-pair binding studies suggest a new binding mode for channel blockers," J. Med. Chem., vol. 52(14), Jan. 2, 2009, pp. 4266-4276.
Zhou, L., et al., "Nilotinib for Imatinib-Resistant or -Intolerant Chronic Myeloid Leukemia in Chronic Phase, Accelerated Phase, or Blast Crisis: A Single- and Multiple-Dose, Open-Label Pharmacokinetic Study in Chinese Patients," Clinical Therapeutics, vol. 31:7, Jul. 2009, pp. 1568-1575.
Zhou, et al., "Correction of Defectrive Protein Trafficking of a Mutant HERG Potassium Channel in Human Long QT Syndrome," The Journal of Biological Chemistry, vol. 274:44, Oct. 29, 1999, pp. 31123-31126.
Rajamani, S., et al., "Drug-induced long QT syndrome: hERG K+ channel block and disruption of protein trafficking by fluoxetine and norfluoxetine," British Journal of Pharmacology, Sep. 11, 2006, vol. 149, pp. 481-489.
Xalkori Package insert, Pfizer Laboratories, revised Feb. 2013, 10 pp.
Yang, Ping, et al., "Allelic Variants in Long-QT Disease Genese in Patients with Drug-Associated Rosades de Pointes," Circulation, Apr. 23, 2002, pp. 1943-1948.

\* cited by examiner

| EXP | FORMULATION FACTORS | 1 | 2 | 3 | 4 |
|---|---|---|---|---|---|
| A | PLGA CONCENTRATION (mg/ml) | 10 | 10 | 10 | 10 |
| B | $LIPID_1/LIPID_2$ MOLAR RATIO | 7:3 | 7:3 | 7:3 | 7:3 |
| C | ORGANIC/AQ VOLUME RATIO | 1 | 1 | 1 | 1 |
| D | DRUG LOADING (mg) | 1 | 1 | 1 | 1 |
| E | $(LIPID_1+LIPID_2)$-(mg) | 2 | 4 | 6 | 8 |

| BATCH NUMBER | AVERAGE PARTICLE SIZE (nm) | DRUG LOADING (%) | ENCAPSULATION EFFICIENCY (%) |
|---|---|---|---|
| 1 | 138.0 | 0.5 | 10 |
| 2 | 117.2 | 0.6 | 12 |
| 3 | 142.7 | 1.0 | 20 |
| 4 | 103.6 | 0.3 | 6 |

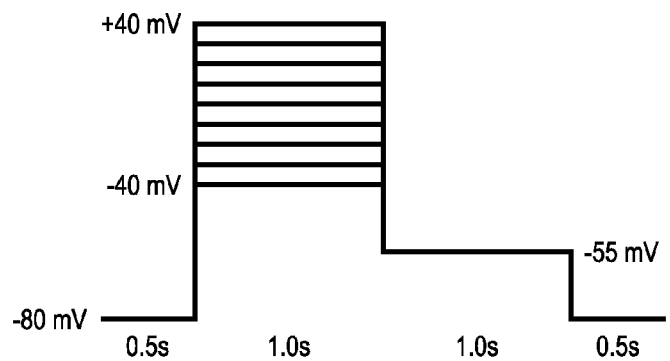
FIG. 11
| | NORMALIZED CURRENT DENSITY | CORRECTED NORMALIZED CURRENT DENSITY | SEM | p value | n= |
|---|---|---|---|---|---|
| BASELINE | 1.000 | 1.000 | N/A | N/A | 3 |
| BATCH A, 6 µM | 0.718 | 0.751 | 0.065 | 0.063 | 3 |
| BATCH A, 12 µM | 0.732 | 0.766 | 0.065 | 0.069 | 3 |
| BATCH A, 18 µM | 0.718 | 0.752* | 0.030 | 0.014 | 3 |
| WASHOUT | 0.439 | 0.473 | 0.027 | 0.175 | 2 |
FIG. 12
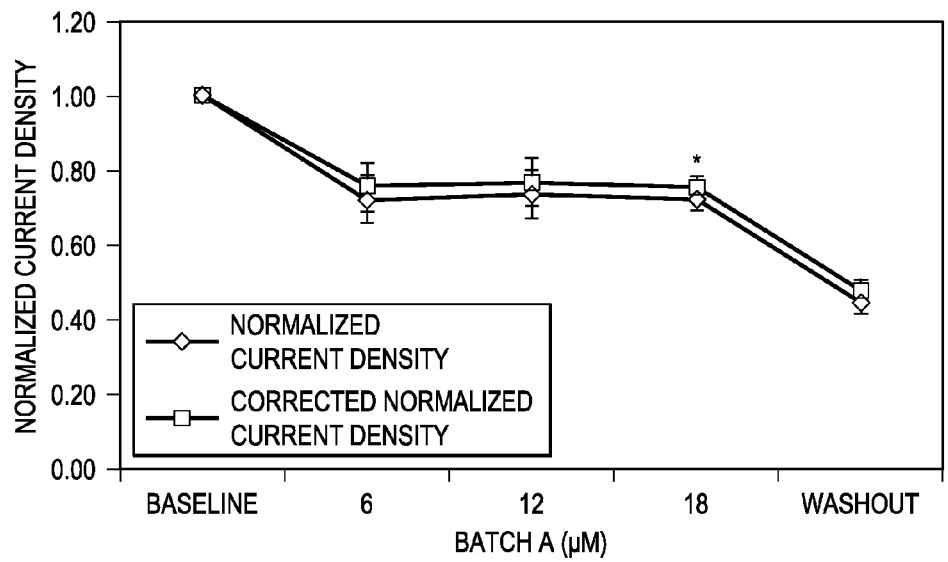
FIG. 13

|  | NORMALIZED CURRENT DENSITY | CORRECTED NORMALIZED CURRENT DENSITY | SEM | p value | n= |
|---|---|---|---|---|---|
| BASELINE | 1.000 | 1.000 | N/A | N/A | 3 |
| BATCH B, 6 μM | 0.840 | 0.873* | 0.019 | 0.023 | 3 |
| BATCH B, 12 μM | 0.877 | 0.911 | 0.133 | 0.572 | 3 |
| BATCH B, 18 μM | 0.565 | 0.598* | 0.092 | 0.022 | 4 |
| WASHOUT | 0.460 | 0.493 | 0.086 | 0.473 | 2 |

|  | NORMALIZED CURRENT DENSITY | CORRECTED NORMALIZED CURRENT DENSITY | SEM | p value | n= |
|---|---|---|---|---|---|
| BASELINE | 1.000 | 1.000 | N/A | N/A | 3 |
| BATCH C, 6 µM | 0.746 | 0.780* | 0.039 | 0.029 | 3 |
| BATCH C, 12 µM | 0.754 | 0.787* | 0.030 | 0.019 | 3 |
| BATCH C, 18 µM | 0.715 | 0.748* | 0.045 | 0.031 | 3 |
| WASHOUT | 0.470 | 0.503 | 0.057 | 0.053 | 2 |

| | NORMALIZED CURRENT DENSITY | CORRECTED NORMALIZED CURRENT DENSITY | SEM | p value | n= |
|---|---|---|---|---|---|
| BASELINE | 1.000 | 1.000 | N/A | N/A | 3 |
| BATCH D, 6 µM | 0.566 | 0.664 | 0.094 | 0.070 | 3 |
| BATCH D, 12 µM | 0.255 | 0.354* | 0.046 | 0.005 | 3 |
| BATCH D, 18 µM | 0.124 | 0.222* | 0.012 | 0.000 | 3 |
| WASHOUT | 0.277 | 0.376 | 0.131 | 0.485 | 2 |

|  | NORMALIZED CURRENT DENSITY | CORRECTED NORMALIZED CURRENT DENSITY | SEM | p value | n= |
|---|---|---|---|---|---|
| BASELINE | 1.000 | 1.000 | N/A | N/A | 3 |
| BATCH E, 6 µM | 0.666 | 0.700* | 0.041 | 0.018 | 3 |
| BATCH E, 12 µM | 0.810 | 0.844 | 0.049 | 0.087 | 3 |
| BATCH E, 18 µM | 0.813 | 0.847 | 0.070 | 0.161 | 3 |
| WASHOUT | 0.628 | 0.662 | 0.181 | 0.275 | 2 |

| COMPOUND TESTED | STATISTICALLY SIGNIFICANT INHIBITION STARTING AT (µM) | MAXIMAL INHIBITION (%) | STATISTICALLY SIGNIFICANT REVERSIBILITY OF THE WASHOUT | CALCULATED $IC_{50}$ (µM) | VOLTAGE DEPENDENCE |
|---|---|---|---|---|---|
| BATCH A | 18 | 24.8 | NO | N/A | YES |
| BATCH B | 6 | 40.2 | NO | N/A | YES |
| BATCH C | 6 | 25.2 | NO | N/A | YES |
| BATCH D | 12 | 77.8 | NO | 8.5 | YES |
| BATCH E | 6 ONLY | 30.0 | NO | N/A | NO |

CURCUMIN-ER, A LIPOSOMAL-PLGA SUSTAINED RELEASE NANOCURCUMIN FOR MINIMIZING QT PROLONGATION FOR CANCER THERAPY

CROSS-REFERENCE TO RELATED APPLICATIONS

This application claims priority to U.S. Provisional Application Ser. No. 61/695,827, filed Aug. 31, 2012, the entire contents of which are incorporated herein by reference.

TECHNICAL FIELD OF THE INVENTION

The present invention relates in general to nanoparticles comprising a polymeric core comprising one or more polymers and one or more active agents and at least one layer of one or more lipids on the surface of the polymeric core. More specifically, the invention relates to the use of curcumin within such a lipid-polymer nanoparticle formulation for minimizing QT prolongation associated with curcumin in treatment of cancer.

STATEMENT OF FEDERALLY FUNDED RESEARCH

None.

BACKGROUND OF THE INVENTION

Without limiting the scope of the invention, its background is described in connection with the delivery of active pharmaceutical agents.

U.S. Pat. No. 7,968,115 to Kurzrock (filed Sep. 7, 2005) is said to provide a compositions and methods for the treatment of cancer, including pancreatic cancer, breast cancer and melanoma, in a human patient. The methods and compositions of the present invention employ curcumin or a curcumin analogue encapsulated in a colloidal drug delivery system, preferably a liposomal drug delivery system. Suitable colloidal drug delivery systems also include nanoparticles, nanocapsules, microparticles or block copolymer micelles. The colloidal drug delivery system encapsulating curcumin or a curcumin analogue is administered parenterally in a pharmaceutically acceptable carrier.

U.S. Pat. No. 8,202,839 to Sung (filed Jan. 7, 2012) is said to disclose a pharmaceutical composition of bioactive nanoparticles composed of chitosan, poly-glutamic acid, and a bioactive agent for oral delivery. The chitosan-based nanoparticles are characterized with a positive surface charge and enhanced permeability for oral drug delivery.

U.S. Patent Application Publication Number 20120058208 by Jacob (Synergistic Composition for Enhancing Bioavailability of Curcumin) (filed Mar. 8, 2012) is said to relate to a composition to enhance the bioavailability of curcumin. In one embodiment, a composition comprising plant extracts of curcumin, vanilla and ginger, wherein the extracts of ginger and vanilla are rich in gingerol and vanillin respectively, is provided. In other embodiments, curcumin, and one or more items selected from the group of vanilla, ginger and capsaicin is provided.

U.S. Patent Application Publication Number 20120003177 by Shen (Curcumin-containing polymers and water-soluble curcumin derivatives as prodrugs of prodrug carriers) (filed Jan. 5, 2012) is said to describe Curcumin, a polyphenol extracted from the rhizome turmeric, that has been polymerized to produce a polymer material having a backbone of one or more repeating structural units, at least one of which comprises a curcumin monomer residue. These curcumin-containing polymers have a wide range of pharmacological activities, including, among others antitumor, antioxidant, anti-inflammatory, antithrombotic and antibacterial activities. Certain species of these polymers have exhibited remarkable antitumor activity. Water-soluble curcumin derivatives and their use as prodrugs and prodrug carriers are also disclosed.

SUMMARY OF THE INVENTION

Problems associated with Curcumin are low solubility, low bioavailability, QT prolongation, and fast in vivo clearance. The advantages of liposomal nanocurcumin are no QT prolongation, high bioavailability, and low in vivo clearance, but the disadvantages are rapid release. The advantages of polymeric nanocurcumin are high bioavailability, sustained release, and low in vivo clearance, but the disadvantages are QT prolongation. The advantages of hybrid nanocurcumin are high bioavailability, sustained release, no QT prolongation, and low in vivo clearance.

The present invention includes methods and compositions comprising a polymeric nanoparticle core comprising one or more polymers and one or more active agents; and at least one layer of one or more lipids on the surface of the polymeric core. The one or more polymers may comprise PLGA; and/or at least one polymer selected from the group consisting of poly(lactic acid), polylactide (PLA), and poly-L-lactide-co-ε-caprolactone (PLCL). In certain aspects, the one or more active agents comprise curcumin or a curcuminoid. The active agent may comprise at least one anti-cancer drug; and/or be selected from at least one of an anti-cancer drug, an antibiotic, an antiviral, an antifungal, an antihelminthic, a nutrient, a small molecule, a siRNA, an antioxidant, and an antibody. In certain aspects, the nanoparticle composition does not cause QT prolongation. In certain aspects, the nanoparticle composition has high bioavailability. In certain aspects, the active agent may comprise a conventional radioisotope. The one or more active agents comprise a water-insoluble dye; and/or a metal nanoparticle, to be used as contrast agents for MRI; and/or be selected from the group comprising Nile red, iron, and platinum. In certain aspects, the one or more lipids comprise 1,2-Dimyristoyl-sn-glycero-3-phosphocholine (DMPC); and/or dimyristoyl phosphatidylglycerol (DMPG); 1,2-dioctadecanoyl-sn-glycero-3-phosphoethanolamine (DSPE), 1,2-distearoyl-sn-glycero-3-phosphoethanolamine-N-[amino(polyethylene glycol) (DSPE-PEG), DMPE PEG Maleimide, Lecithin, cholesterol, 1,2-dimyristoyl-sn-glycero-3-phosphoethanolamine-N-(lissamine rhodamine B sulfonyl) (ammonium salt), and 1,2-dimyristoyl-sn-glycero-3-phosphoethanolamine-N-(7-nitro-2-1,3-benzoxadiazol-4-yl) (ammonium salt). In various aspects, the nanoparticle composition may comprise DMPC and DMPG in a molar ratio of 9:1, 7:3, 8:2, or 7.5:2.5. In certain aspects, the nanoparticles may comprise at least one targeting agent, wherein the targeting agent selectively targets the nanoparticle to diseased tissue/cells, thereby minimizing whole body dose; and/or wherein the targeting agent comprises an antibody or functional fragment thereof that is capable of recognizing a target antigen; and/or selected from the group consisting of an antibody, a small molecule, a peptide, a carbohydrate, an siRNA, a protein, a nucleic acid, an aptamer, a second nanoparticle, a cytokine, a chemokine, a lymphokine, a receptor, a lipid, a lectin, a ferrous metal, a magnetic particle, a linker, an isotope and combinations thereof. In certain aspects, the nanoparticles have a size of 90 to 150 nm. The bioavailability of the active agent may be increased, a QT prolongation is reduced, and the active agent may be released in a sustained manner.

The invention includes embodiments of methods for forming a nanoparticle composition comprising forming an organic phase by combining one or more polymers, one or more solvents and one or more active agents; forming a lipid aqueous phase by mixing one or more lipids with water; mixing the organic phase with the lipid aqueous phase, whereby an emulsion is formed; and incubating the emulsion, whereby self-assembly of nanoparticles occurs. The one or more polymers may comprise PLGA; and/or at least one polymer selected from the group consisting of poly(lactic acid), polylactide (PLA), and poly-L-lactide-co-ϵ-caprolactone (PLCL). The organic phase may comprise PLGA in a concentration of 2-90 mg/ml; and/or curcumin in a concentration of 1-15 weight/volume %. In various aspects, the one or more solvents may comprise an organic solvent; acetonitrile; at least one solvent selected from the group consisting of Acetone, tert butyl alcohol, Dimethyl formamide, and Hexafluoro isopropanol. The one or more active agents comprise curcumin or a curcuminoid; and/or at least one anti-cancer drug; and/or a conventional radioisotope; and/or at least one active agent selected from the group consisting of selected from the group comprising Nile red, iron, and platinum. In certain aspects, the one or more lipids may comprise DMPC; and/or DMPG, and/or at least one lipid selected from the group consisting of 1,2-dioctadecanoyl-sn-glycero-3-phosphoethanolamine (DSPE), 1,2-distearoyl-sn-glycero-3-phosphoethanolamine-N-[amino(polyethylene glycol) (DSPE-PEG), DMPE PEG Maleimide, Lecithin, cholesterol, 1,2-dimyristoyl-sn-glycero-3-phosphoethanolamine-N-(lissamine rhodamine B sulfonyl) (ammonium salt), and 1,2-dimyristoyl-sn-glycero-3-phosphoethanolamine-N-(7-nitro-2-1,3-benzoxadiazol-4-yl) (ammonium salt). In certain aspects, the one or more lipids comprise DMPC and DMPG in a molar ratio of 9:1, 7:3, 8:2, 7.5:2.5. In certain aspects, mixing the organic phase with the lipid aqueous phase comprises slowly stirring the organic phase into the lipid aqueous phase; and/or mixing the organic phase with the lipid aqueous phase comprises vortexing; and/or mixing the organic phase with the lipid aqueous phase further comprises sonicating. In certain aspects, incubating the emulsion comprises stirring the emulsion for 2 hours. In certain aspects, the method may further comprise separating the nanoparticles after incubating the emulsion; and/or filtering the nanoparticles after incubating the emulsion; and/or freezing the nanoparticles; and/or lyophilizing the nanoparticles; and/or attaching a targeting agent to the nanoparticles; and/or attaching at least one targeting agent, wherein the targeting agent selectively targets the nanoparticle to diseased tissue/cells, thereby minimizing whole body dose; and/or attaching at least one targeting agent to the nanoparticles, wherein the targeting agent comprises an antibody or functional fragment thereof that is capable of recognizing a target antigen. In certain aspects, the nanoparticles have a size of 90 to 150 nm.

The invention includes embodiments of pharmaceutical agents comprising a nanoparticle for drug delivery comprising a polymer, an active agent and at least one layer of one or more lipids encapsulating the polymer and the active agent.

The invention includes embodiments for treating a patient suspected of being afflicted with a disease comprising administering nanoparticles, wherein the nanoparticles comprise a polymeric core comprising one or more polymers and one or more active agents and at least one layer of one or more lipids on the surface of the polymeric core. In certain aspects, administering nanoparticles comprises administering the nanoparticle by intramuscular, subcutaneous, intravascular, or intravenous administration. Disease can be selected from the group consisting of neurologic, oncologic, and metabolic diseases; and/or from the group consisting of Parkinson's disease, Alzheimer's disease, multiple sclerosis, ALS, sequel, behavioral and cognitive disorders, autism spectrum, depression, and neoplastic disease; and/or cancer. In certain aspects, the active agent is released in a sustained manner.

The invention includes embodiments of composition comprising a polymeric nanoparticle core comprising one or more polymers and curcumin and at least one layer of one or more lipids on the surface of the polymeric core.

The invention includes embodiments of forming a nanoparticle composition comprising forming an organic phase by combining one or more polymers, one or more solvents and curcumin; forming a lipid aqueous phase by mixing one or more lipids with water; mixing the organic phase with the lipid aqueous phase, whereby an emulsion is formed; and incubating the emulsion, whereby self-assembly of nanoparticles occurs.

The invention includes embodiments of pharmaceutical agents comprising a nanoparticle for drug delivery comprising a polymer, curcumin, and at least one layer of one or more lipids encapsulating the polymer and the active agent.

The invention includes embodiments of methods for treating a patient suspected of being afflicted with a disease, the method comprising administering nanoparticles, wherein the nanoparticles comprise a polymeric core comprising one or more polymers, curcumin, and at least one layer of one or more lipids on the surface of the polymeric core.

Another embodiment includes a composition for treating cancer comprising: a polymeric nanoparticle core comprising one or more polymers and at least one of curcumin or curcuminoids; and at least one layer of one or more lipids on the surface of the polymeric core, wherein the at least one of the curcumin or curcuminoids nanoparticles, wherein the composition does not cause QT prolongation when provided to a subject. In one aspect, the one or more polymers comprise at least one of poly(lactic-co-glycolic acid) (PLGA), poly(lactic acid), polylactide (PLA), or poly-L-lactide-co-ϵ-caprolactone (PLCL).

Another embodiment includes a method of forming a nanoparticle composition comprising: forming an organic phase by combining one or more polymers, one or more solvents and at least one of curcumin or curcuminoids; forming a lipid aqueous phase by mixing one or more lipids with water; mixing the organic phase with the lipid aqueous phase, whereby an emulsion is formed; and incubating the emulsion, whereby self-assembly of nanoparticles occurs and wherein the curcumin or curcuminoids nanoparticles does not cause QT prolongation when provided to a subject.

Another embodiment includes a method for treating a patient suspected of being afflicted with a disease comprising administering nanoparticles, wherein the nanoparticles comprise a polymeric core comprising one or more polymers and one or more active agents and at least one layer of one or more lipids on the surface of the polymeric core, wherein the active agent is suspected of causing QT prolongation when provided to a subject. In one aspect, the method also includes the step of administering the nanoparticle by intramuscular, subcutaneous, intravascular, or intravenous administration.

Another embodiment includes a method of forming a nanoparticle that prevents the active agent from causing QT prolongation composition comprising: forming an organic phase by combining one or more polymers, one or more solvents and the active agent that causes QT prolongation; forming a lipid aqueous phase by mixing one or more lipids with water; mixing the organic phase with the lipid aqueous phase, whereby an emulsion is formed; and incubating the emulsion, whereby self-assembly of nanoparticles occurs.

Another embodiment includes a pharmaceutical agent comprising: a nanoparticle for drug delivery comprising a polymer, an active agent that causes QT prolongation, and at least one layer of one or more lipids encapsulating the polymer and the active agent and the agent does not cause QT prolongation.

Another embodiment includes a method for treating a patient suspected of being afflicted with a disease, the method comprising administering nanoparticles, wherein the nanoparticles comprise a polymeric core comprising one or more polymers, curcumin, and at least one layer of one or more lipids on the surface of the polymeric core, wherein treating the patient does not cause QT prolongation.

In another embodiment, the method of treating a subject suspected of having cancer includes: identifying that a patient suspected of having a cancer; and Providing the subject with an amount of at least one or curcumin or curcuminoids in an amount sufficient to reduce the cancer in the subject, wherein the at least one or curcumin or curcuminoids are in a polymeric nanoparticle core comprising one or more polymers and at least one of curcumin or curcuminoids; and at least one layer of one or more lipids on the surface of the polymeric core, wherein the at least one of the curcumin or curcuminoids nanoparticles does not cause QT prolongation when provided to a subject. In one aspect, the cancer is a pancreatic, prostate or breast cancer.

BRIEF DESCRIPTION OF THE DRAWINGS

For a more complete understanding of the features and advantages of the present invention, reference is now made to the detailed description of the invention along with the accompanying figures and in which:

FIG. 4A shows formulations of hybrid nanocurcumin (HNC). Demonstrated are four different formulations of HNC using different ratio of DMPC and DMPG. FIG. 4B shows particle size distribution of Batch 3.

FIG. 11 shows the pulses protocol or the original data acquisition design: Acquisition Rate(s): 1.0 kHz FIG. 12 shows the effect of batch A on hERG current density from transfected HEK 293 cells at 20 my.

FIG. 13 shows the effect of batch A on hERG current density from transfected HEK 293 cells at 20 mV.

DETAILED DESCRIPTION OF THE INVENTION

Figure 1:
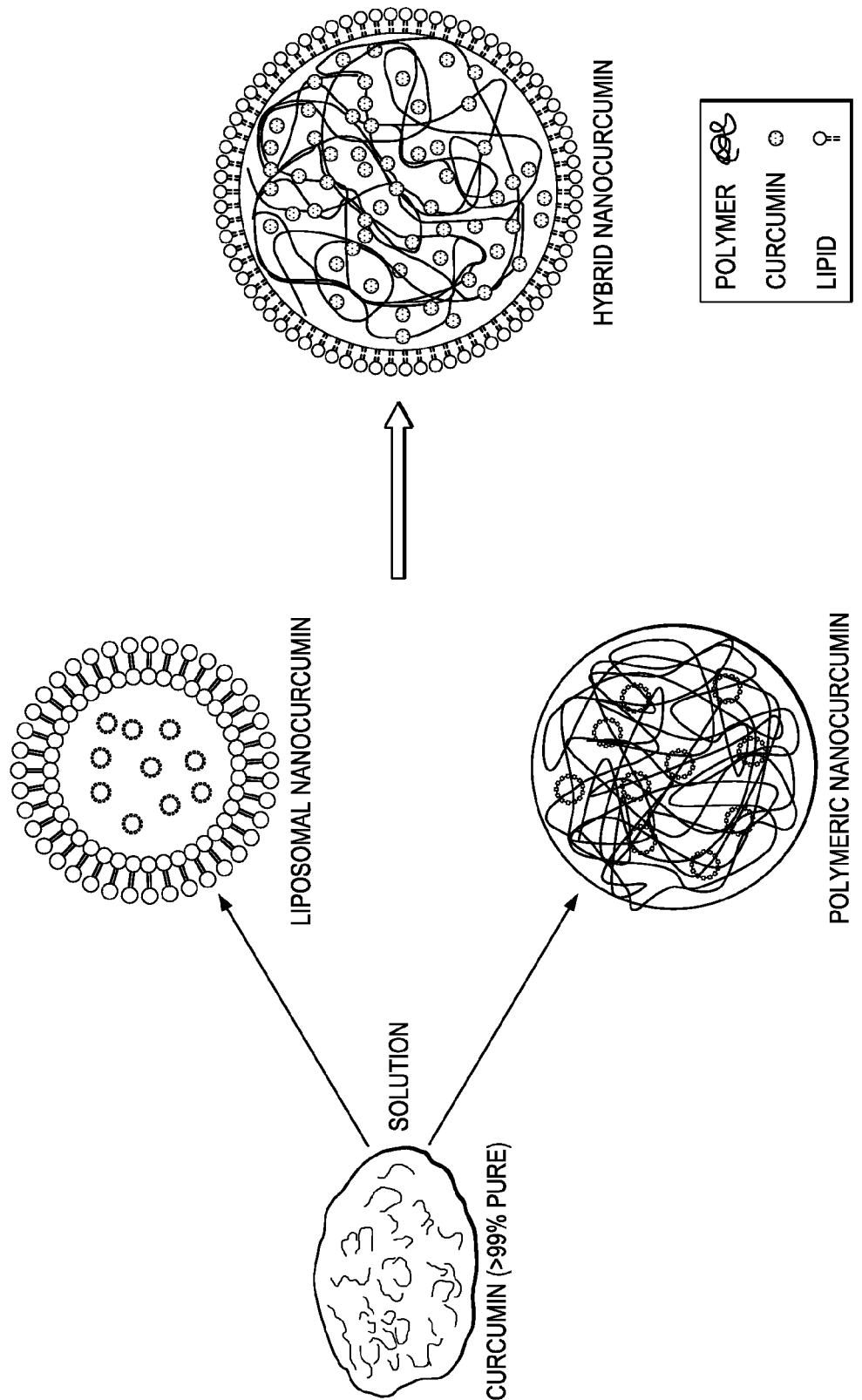
FIG. 1 depicts the basic concept of hybrid nanocurcumin (HNC) formation; Lipids-DMPC and DMPG. Problems associated with Curcumin are low solubility, low bioavailability, QT prolongation, and fast in vivo clearance. The advantages of liposomal nanocurcumin are no QT prolongation, high bioavailability, and low in vivo clearance, but the disadvantages are rapid release. The advantages of polymeric nanocurcumin are high bioavailability, sustained release, and low in vivo clearance, but the disadvantages are QT prolongation. The advantages of hybrid nanocurcumin are high bioavailability, sustained release, no QT prolongation, and low in vivo clearance.
Figure 2:
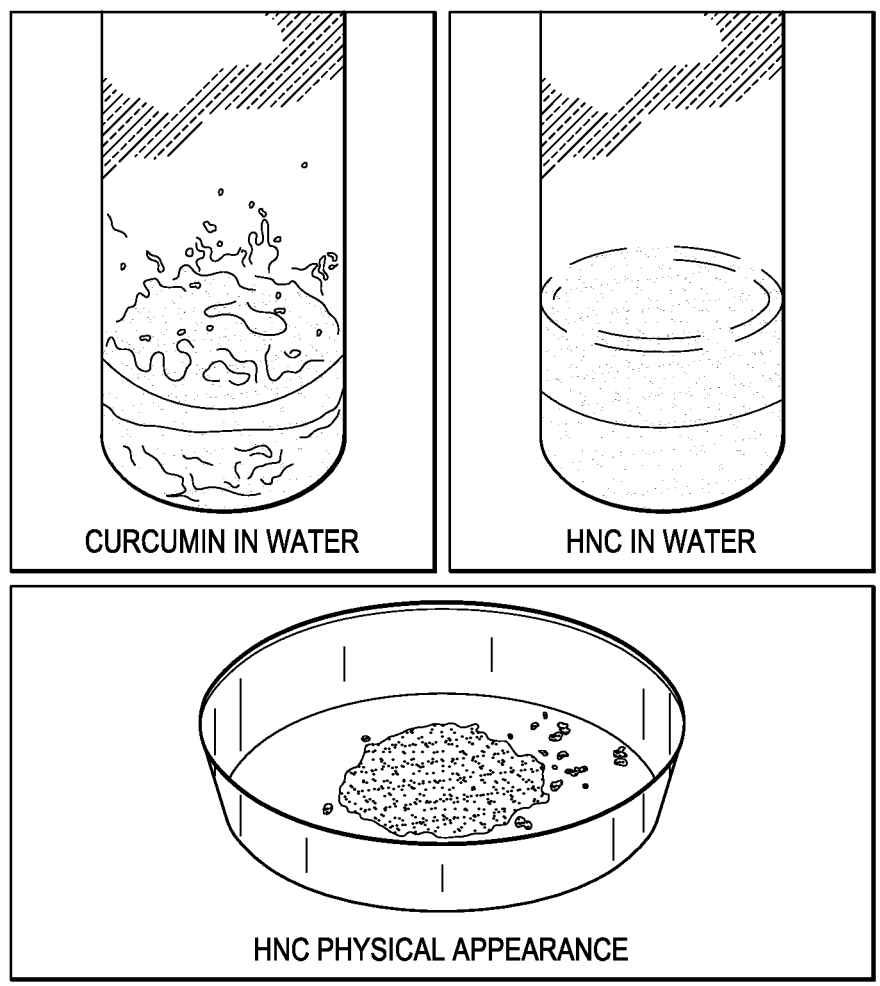
FIG. 2 demonstrates improved dispersibility in water with HNC.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Problems associated with Curcumin are low solubility, low bioavailability, QT prolongation, and fast in vivo clearance. The advantages of liposomal nanocurcumin are no QT prolongation, high bioavailability, and low in vivo clearance, but the disadvantages are rapid release. The advantages of polymeric nanocurcumin are high bioavailability, sustained release, and low in vivo clearance, but the disadvantages are QT prolongation. The advantages of hybrid nanocurcumin are high bioavailability, sustained release, no QT prolongation, and low in vivo clearance.

A requirement in commercial drug development is to assay drug effects on hERG (Ikr) in in vitro assays using transfected KEK293 cells. The present inventors determined anti-hERG activity of curcumin (diferuloylmethane) in DMSO, and of three formulated curcumin compounds: liposomal curcumin, nanocurcumin, and a sustained release PLGA curcumin. The present inventors recognize that the K+ current $IC_{50}$ of curcumin formulated in DMSO is 3.4 uM. Considered within the context of current clinical Phase 1a pharmacokinetics in normal subjects where blood plasma levels range between 5-11 uMol, following a two hour infusion of 4.5 mg/kg, intravenous, or subcutaneous curcumin formulations for therapeutic applications can inhibit IKr, lead to Torsade de Points, and possible clinical mortality. However, neither the liposomal, nor the nanocurcumin formulation at 12 uMol exhibits this effect on the K+ channel. The co-administration of empty liposomes to curcumin was equally effective in prohibiting the hERG blockade, however, the PLGA-curcumin formulation lacked this effect.

These observations are one basis for (constructing) a new curcumin formulation consisting of liposome and PLGA, which allows sustained release of curcumin without the associated cardiac K+ channel inhibitory properties of curcumin.

The treatment of cancer is limited by the side effects of the anti-cancer drugs. Chemotherapy is the only available option for the treatment of advanced cancers. However, increasing evidences of drug resistance and non-specific toxicity of these agents limits their therapeutic outcomes. To overcome this problem it is important to deliver the drug at the site of cancer in the body in the right amount. A novel way to approach this problem is through targeted drug delivery system, which preferentially delivers the drug to the site of cancer. In certain embodiment, targeting molecules (e.g., antibodies) that recognize the cancer cells and direct the drug containing tiny spherical particles (nanoparticles) to the cancer cells are used.

In certain embodiments, at least one targeting agent is attached to the nanoparticles, wherein the targeting agent comprises an antibody or functional fragment thereof that is capable of recognizing a target antigen. The targeting agents may be attached by insertion of hetero/homo bifunctional spacer capable of reacting with amines of lipids and targeting moieties.

Curcumin is a potent anticancer agent and is being used for its pharmacological action for last few decades. However, the major problems associated with curcumin are (1) low systemic bioavailability following administration via any route; (2) curcumin alone brings about QT prolongation; and (3) fast in vivo clearance of curcumin. The present inventors solved these problems by formulating curcumin (99% pure) into a hybrid nanoformulation. See FIG. 1.

The present inventors recognized that a nanoformulation provides the solutions to increase bioavailability and that liposome formulation of curcumin show almost no QT prolongation. But such formulations lack stability and possess some inherent toxicity at higher doses. The present inventors recognize that curcumin has a very rapid clearance when administered in animal models.

The present inventors have developed a nanoformulation system that increases the bioavailability of curcumin, minimizes the QT prolongation, and releases the drug curcumin in a sustained manner.

The hybrid nanocurcumin (HNC) system is a hybrid of lipids and polymer wherein the polymeric core encapsulates curcumin. The lipid is present as a continuous layer on the surface of the polymeric nanoparticle. In other word, the lipid cases the polymeric nanoparticle. The lipid component of the hybrid nanocurcumin helps in reducing the QT prolongation while the polymeric core of the hybrid system facilitates the release of curcumin in a sustained manner. The hybrid nanocurcumin (HNC) system solved all the above-mentioned problems of (1) bioavailability of curcumin, (2) QT prolongation due to curcumin and (3) sustained release of curcumin simultaneously.

The advantages of hybrid nanocurcumin (HNC) system are: (1) in vivo bioavailability of active agents (e.g., curcumin) is improved; (2) the lipid component of the hybrid nanocurcumin reduces QT prolongation; (3) the polymeric core of the hybrid system facilitates the release of the active agent (e.g., curcumin) in a sustained manner; (4) the formulation itself is simple, convenient one-step process; and (5) this system can be used to formulate other similar type of drugs or active agents, which may comprise hydrophobic molecules. Examples would include curcumin analogues, docetaxel, paclitaxel etc.

The commercial potentials of hybrid nanocurcumin formulation are enormous due to better bioavailability and reduced side effects.

An embodiment is a Liposomal-Curcumin-PLGA sustained release compound for prevention and treatment of neurologic, oncologic, or metabolic diseases (Hybrid Nanocurcumin formulation).

Certain embodiments can be described as intravenous and/or subcutaneous administration of a novel formulation of synthesized curcumin (diferuloylmethane) bound to PLGA and a liposome. Such formulation is designed to offer a sustained release of curcumin as active agent. Reference is made to the prevention of cardiac events due to the incorporation of a liposomal component of the formulation.

In further embodiments the compositions may be used for the treatment of neurologic-auto-immunological degenerative diseases (Parkinson's disease, Alzheimer's disease, multiple sclerosis, ALS, sequel, behavioral and cognitive disorders, autism spectrum, and depression), neoplastic diseases (cancer).

In certain embodiments the compositions of the present invention are administered intramuscular, subcutaneous and or intravascular.

Certain embodiments comprise curcumin (diferuloylmethane)-encapsulated in a liposomal-PLGA envelope designated hybrid nanocurcumin formulation.

In one embodiment, the active agent is curcumin, which is a potent natural anticancer agent, is employed in a nanoparticle-based delivery system. One limitation is the QT prolongation effect of curcumin, even when it is associated with nanoparticle-based systems. This makes it difficult to pass FDA standards for commercial use. The hybrid nanocurcumin formulation solves this problem and reduces QT prolongation effect of curcumin, which makes it ideal for commercial application. In addition, the hybrid nanocurcumin formulation releases curcumin in a sustained manner, which improves the systemic availability and decreases fast clearance of curcumin in animal models. Therefore, the hybrid nanocurcumin formulation can directly be used to produce nanotechnology based hybrid dosage forms for curcumin. In other embodiments curcumin may be replaced by a variety of similar drugs or active agents. Such compositions may directly go into production by pharmaceutical companies to test for phase I and phase II.

Example 1

Hybrid Nanocurcumin Formulation: PLGA was dissolved in organic solvent, acetonitrile to get a concentration of 10 mg/ml. Curcumin (5%) was dissolved in this polymer-organic solvent phase. Lipids (DMPC and DMPG) were mixed in a different molar ratios and volume was made up to 1 ml. In more detail:

Hybrid Nanocurcumin Formulation: Polymer PLGA (10 mg) was dissolved in 1 ml of organic solvent, acetonitrile to get a concentration of 10 mg/ml. Curcumin (5% with respect to polymer) was dissolved in this polymer-organic solvent mixture. Lipids (DMPC and DMPG) were mixed in different molar ratios, and it was found that a ratio DMPC/DMPG=7.5/2.5 gave the best particles. DMPC (lipid 1) was dissolved in 4% ethanol in water. DMPG (lipid 2) was dissolved in water and volume was made up to 1 ml. These solutions were mixed and heated to obtained transparent solutions. Total lipid content with respect to polymer was varied from 2 mg to 8 mg. The organic phase was slowly stirred into the lipid aqueous phase keeping the organic to aqueous volume ratio at 1:1. The emulsion was vortexed for 30 sec and then sonicated for 5 min. The whole emulsion system was then stirred for 2-3 hours for self-assembly. This was then filtered thrice using Amicon filter (10 KD cutoff). The hybrid particles thus obtained were flash frozen using liquid nitrogen and lyophilized overnight. These were stored at −20° C. until further used.

The organic phase was slowly stirred into the lipid aqueous phase keeping the organic to aqueous volume ratio at 1:1. The emulsion was vortexed for 30 sec and then sonicated for 5 min. The whole emulsion system was then stirred for 2 hours for self-assembly. This was then filtered thrice using Amicon filter (10 KD cutoff). The hybrid particles thus obtained were flash frozen using liquid nitrogen and lyophilized overnight. These were stored at −20° C. until further used.

Figures 4A, 4B, 5:
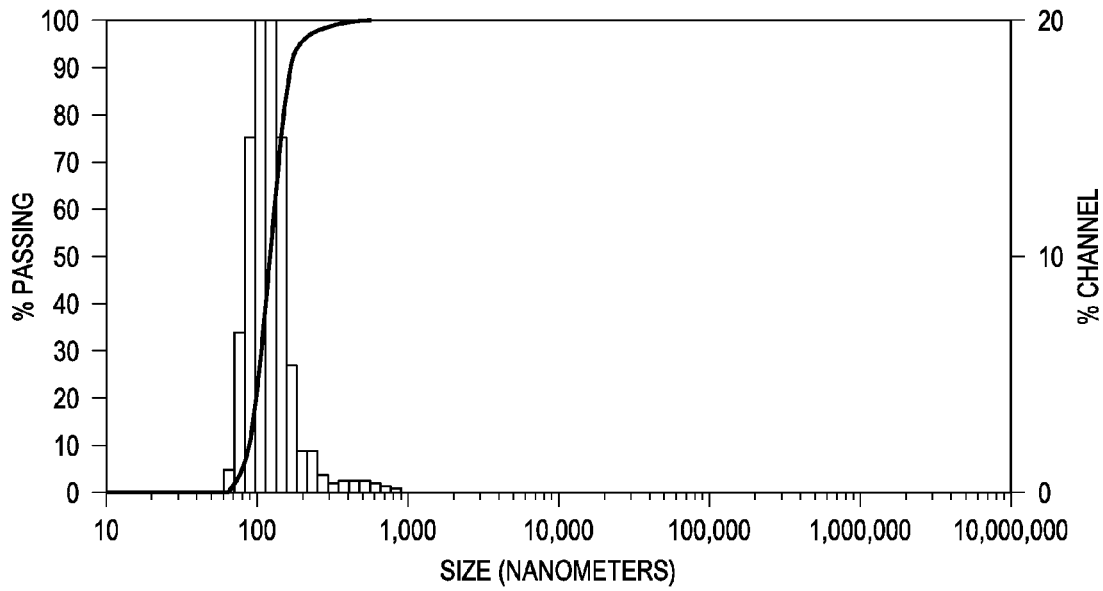
FIGS. 4A and 4B.
FIG. 5 shows HNC characterization, including average particle size, drug loading, and encapsulation efficiency.

Hybrid Nanocurcumin Characterization: The hybrid nanoparticles were characterized for particle size, drug loading, encapsulation efficiency and surface morphology. FIG. 4A shows results from one set of studies where the total amounts of lipids were varied keeping the molar ratio of two lipids constant. In other studies, lipids (DMPC and DMPG) were mixed in different molar ratios and we found that DMPC/DMPG::7.5/2.5 gave the best particles. In certain embodiments, the Hybrid Nanocurcumin is referred to herein as Curcumin ER.

Particle size distribution: The particle size distribution is shown in FIG. 4B. The particle sizes for various batches post lyophilization are listed in Table 1. Particle size analysis of the lyophilized nanoparticles was carried out using a Nanotrac system (Mircotrac, Inc., Montgomeryville, Pa., USA). The lyophilized nanoparticles were dispersed in double distilled water and vortexed at high for 10 sec and then measured for particle size. The results were reported as the average of three runs with triplicate runs in each run.

TABLE 1

Average particle size distributions for all batches

| Batch | DMPC + DMPG (mg) | Av. Particle Size (nm) |
|---|---|---|
| Batch 1 | 2 | 138.0 |
| Batch 2 | 4 | 117.2 |
| Batch 3 | 6 | 142.7 |
| Batch 4 | 8 | 103.6 |

Drug loading and encapsulation efficiency: The hybrid nanocurcumin was dissolved in acetonitrile and drug loading and encapsulation efficiency was determined by spectrophotometry. Values are listed in Table 2. Lyophilized hybrid nanoparticles (5 mg) was dissolved in 2 ml acetonitrile to extract curcumin into acetonitrile for determining the encapsulation efficiency. The samples in acetonitrile were gently shaken on a shaker for 4 h at room temperature to completely extract out curcumin from the nanoparticles into acetonitrile. These solutions were centrifuged at 14,000 rpm (Centrifuge 5415D, Eppendorf AG, Hamburg, Germany) and supernatant was collected. Suspension (20 µl) was dissolved in ethanol (1 ml) and was used for the estimations. The curcumin concentrations were measured spectrophotometrically at 450 nm. A standard plot of curcumin (0-10 µg/ml) was prepared under identical conditions.

The encapsulation efficiency (EE) of PLGA-CURC was calculated using $$\text{Encapsulation efficiency (\%)} = \frac{\text{Total drug content in nanoparticles}}{\text{Total drug amount}} \times 100$$

The percent drug loading was calculated by total amount of drug extracted from the hybrid nanoparticles to the known weight of nanoparticles $$\text{Drug loading(\%)} = \frac{\text{Drug content}}{\text{Weight of nanoparticles}} \times 100$$

TABLE 2

Drug loading and encapsulation efficiency for all batches.

| Batch | Drug Loading (%) | Encapsulation efficiency (%) |
|---|---|---|
| Batch 1 | 0.5 | 10 |
| Batch 2 | 0.6 | 12 |
| Batch 3 | 1.0 | 20 |
| Batch 4 | 0.3 | 6 |

Figure 3:
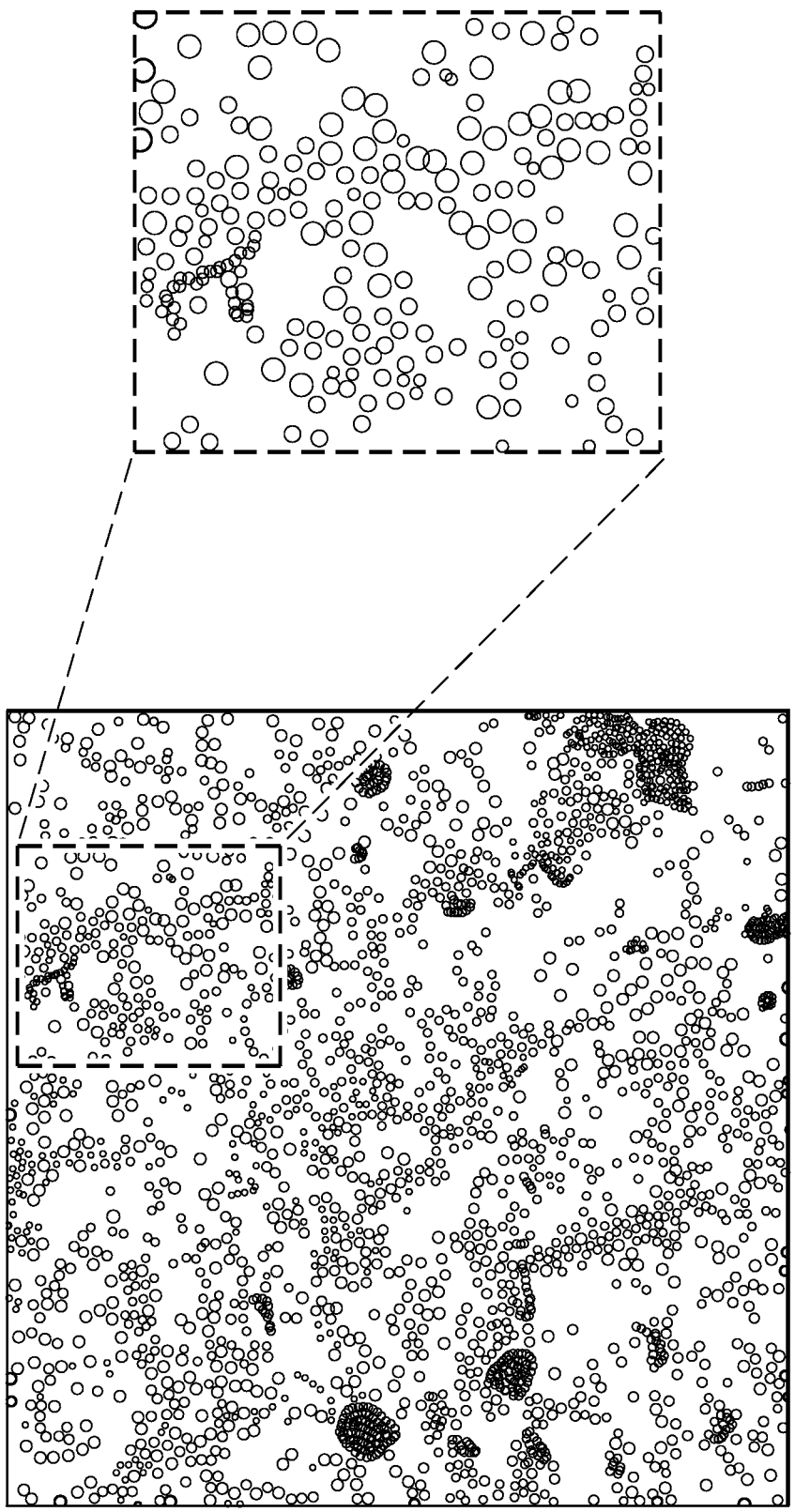
FIG. 3 represents transmission electron micrographs showing HNC. The TEM scan shows HNC as spherical smooth nanoparticles with uniform size.

Surface morphology: Surface morphology of the HNC was determined by Transmission electron microscopy. The TEM scan is shown below in FIG. 3. The surface morphology of the hybrid nanoparticle was studied using transmission electron microscopy, (TEM). A small quantity of aqueous solution of the lyophilized hybrid nanoparticles (1 mg/ml) was placed on a TEM grid surface with a filter paper (Whatman No. 1). One drop of 1% uranyl acetate was added to the surface of the carbon-coated grid. After 1 minute of incubation, excess fluid was removed and the grid surface was air dried at room temperature. It was then loaded into the transmission electron microscope (LEO EM910, Carl Zeiss SMT Inc, NY, USA) attached to a Gatan SC 1000 CCD camera. HNC are characterized, which included determination of average particle size, drug loading, and encapsulation efficiency and results are shown in FIG. 5.

Figure 8:
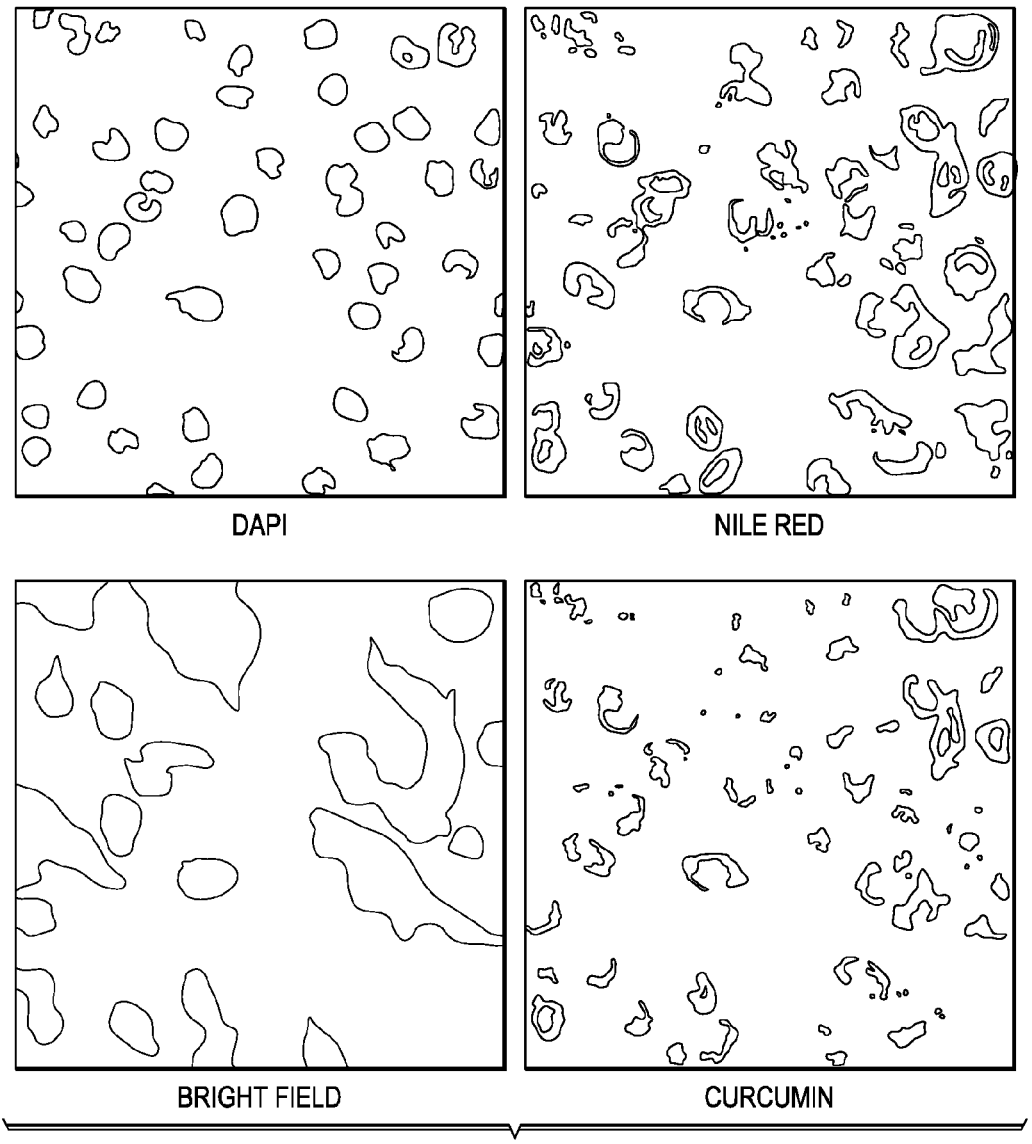
FIG. 8 shows intracellular uptake of HNC in MiaPaCa cells.

Hybrid Nanocurcumin Evaluation: Hybrid nanocurcumin was evaluated by intracellular uptake and MTT assays. This study shows robust uptake of HNC within 1 hour in pancreatic cancer cell, MiaPaCa cells as shown in FIG. 8. Intracellular uptake of nanoparticle was determined in pancreatic, prostate and breast cancer cells using a Confocal Laser Scanning Microscope (CLSM). For these studies, cells were placed on a cover slip in a 6-well tissue culture plate and incubated at 37° C. until they reached sub-confluent levels. The cells were then exposed to 100 μg/ml concentrations of fluorescent nile red labeled hybrid nanoparticles. After 2 hrs of incubation, cells were viewed under the microscope.

Figure 10:
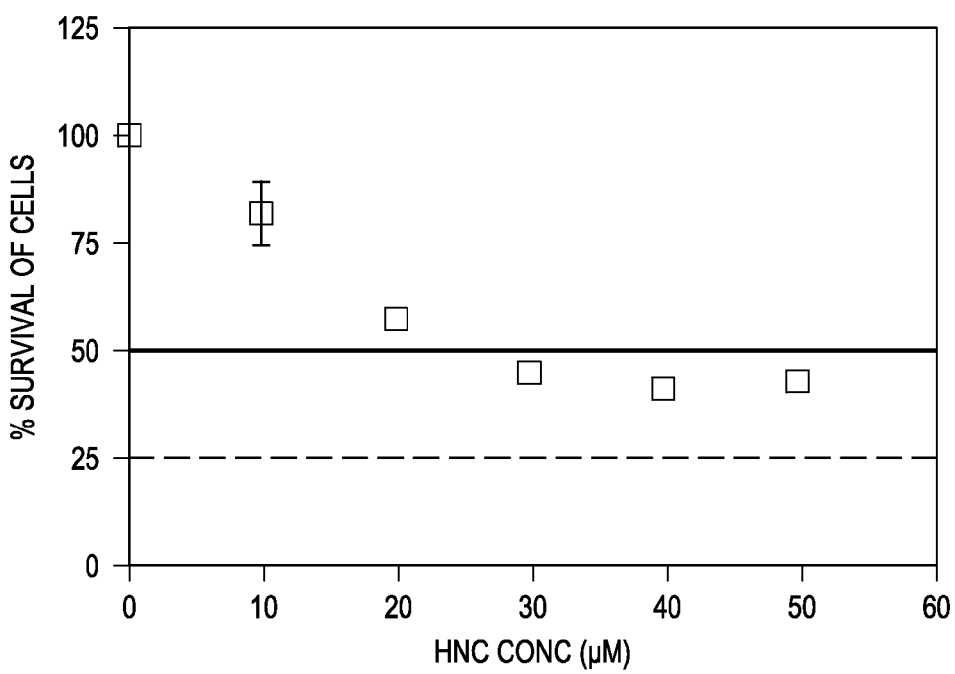
FIG. 10 shows MTT cell viability using HNC employing a pancreatic cancer cell line (MiaPaCa cell line) at 48 hours.
Figures 14, 15:
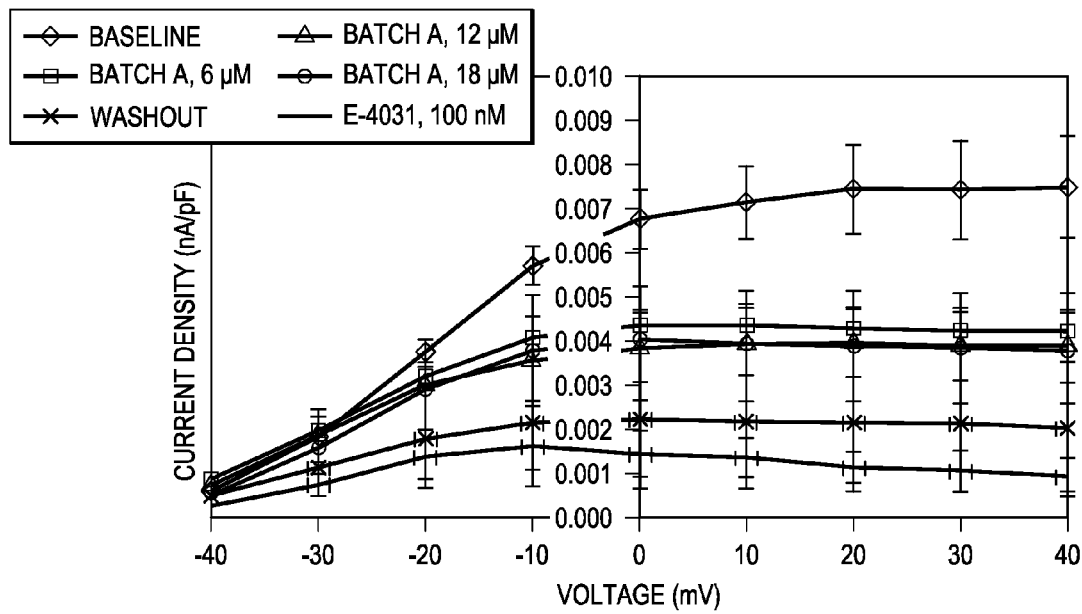
FIG. 14 shows the relationship (I-V) of hERG current amplitude from transfected HEK 293 cells exposed to Batch A.
FIG. 15 shows the effect of batch B on hERG current density from transfected HEK 293 cells at 20 mV.
Figure 16:
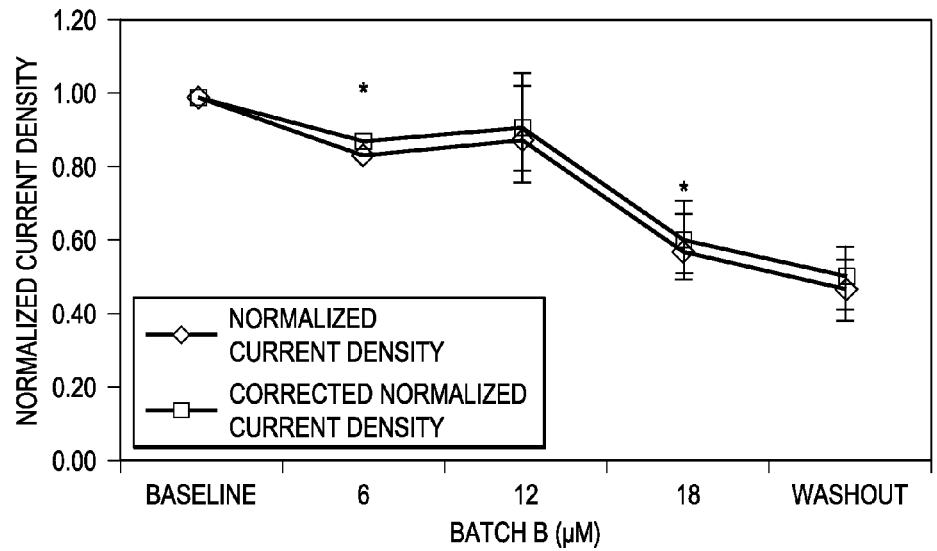
FIG. 16 shows the effect of batch B on hERG current density from transfected HEK 293 cells at 20 mV.
Figure 17:
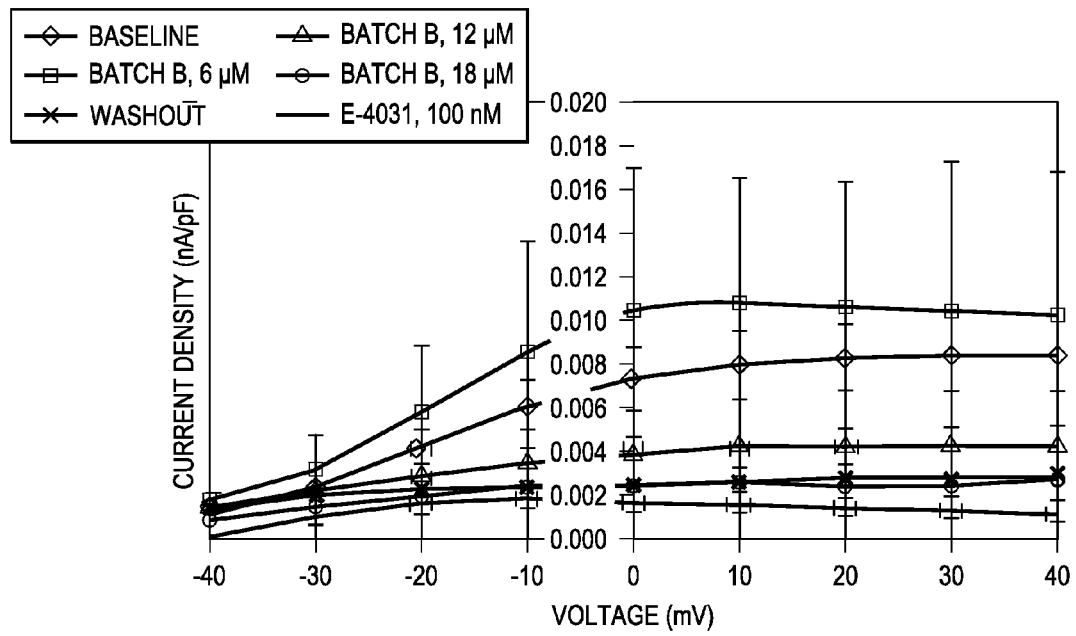
FIG. 17 shows the relationship (I-V) of hERG current amplitude from transfected HEK 293 cells exposed to Batch B.
Figures 18, 19:
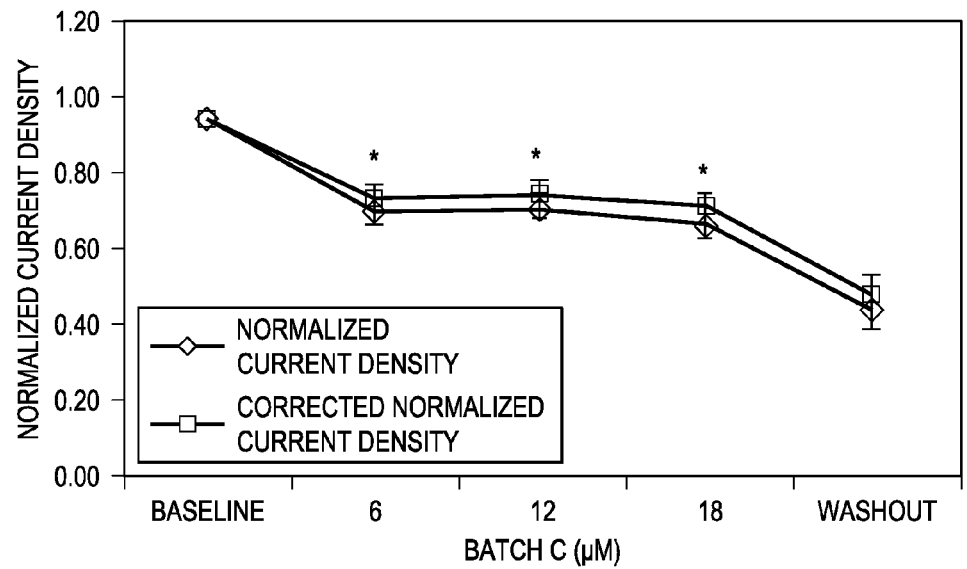
FIG. 18 shows the effect of batch C on hERG current density from transfected HEK 293 cells at 20 mV.
FIG. 19 shows the effect of Batch C on hERG current density from transfected HEK 293 cells at 20 mV.
Figures 20, 21:
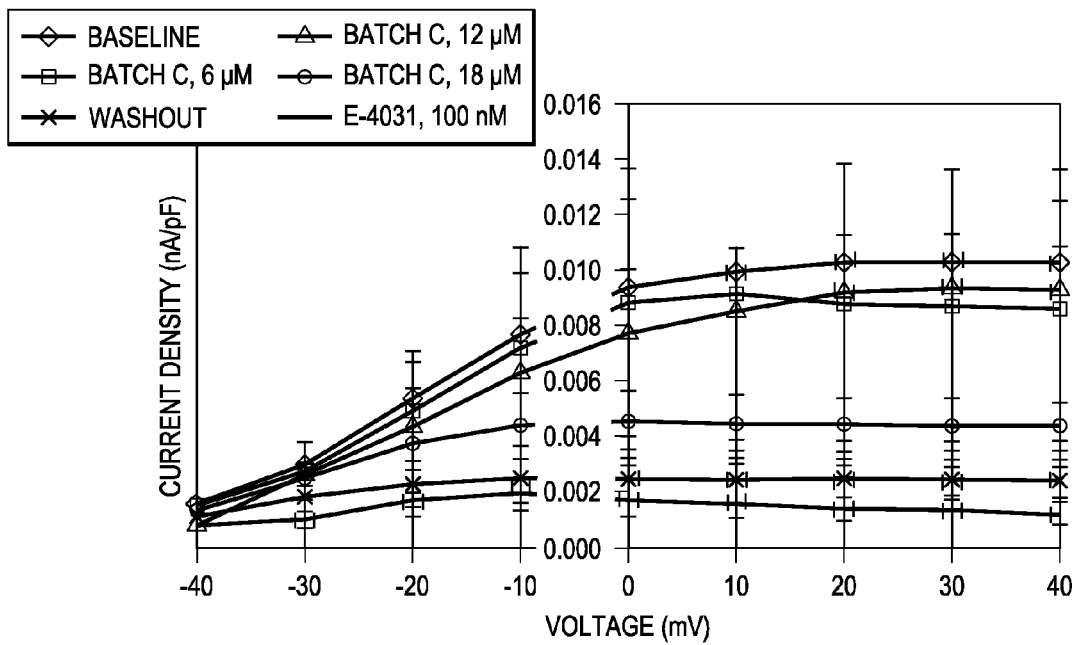
FIG. 20 shows the relationship (I-V) of hERG current amplitude from transfected HEK 293 cells exposed to Batch C.
FIG. 21 shows the effect of batch D on hERG current density from transfected HEK 293 cells at 20 mV.
Figure 22:
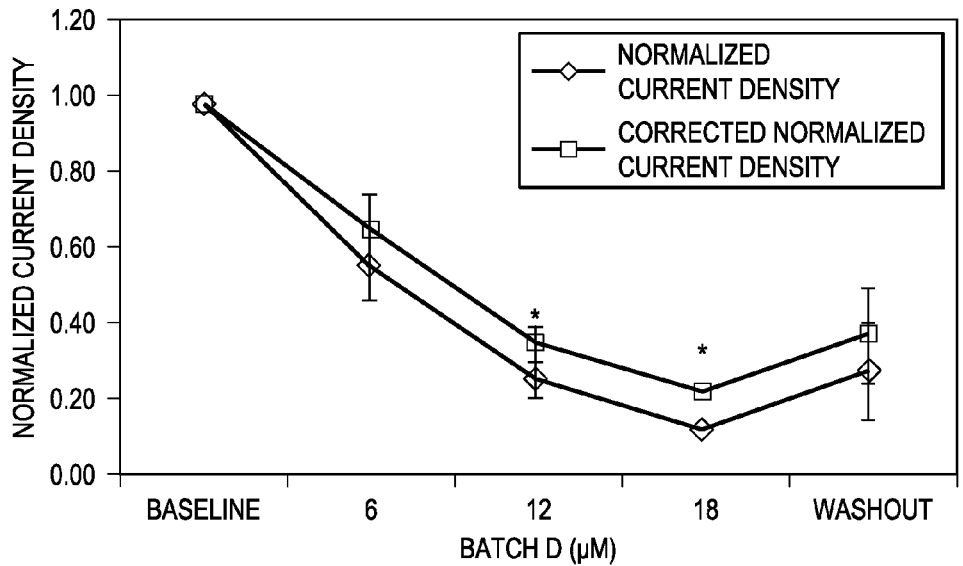
FIG. 22 shows the effect of batch D on hERG current density from transfected HEK 293 cells at 20 mV.
Figure 23:
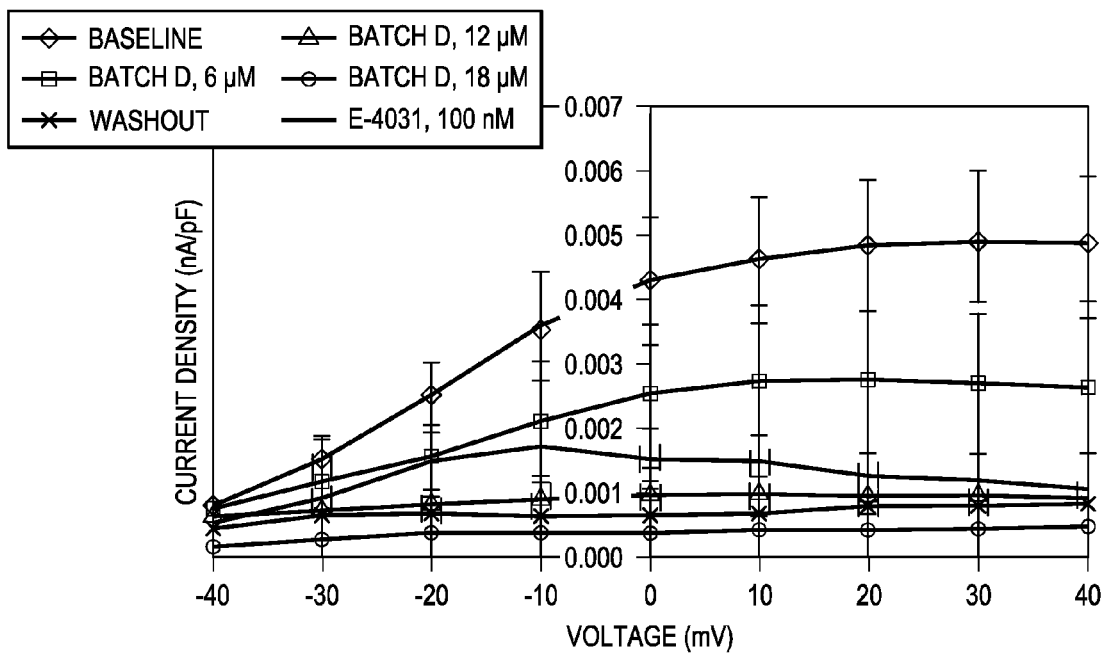
FIG. 23 shows the relationship (I-V) of hERG current amplitude from transfected HEK 293 cells exposed to Batch D.
Figures 24, 25:
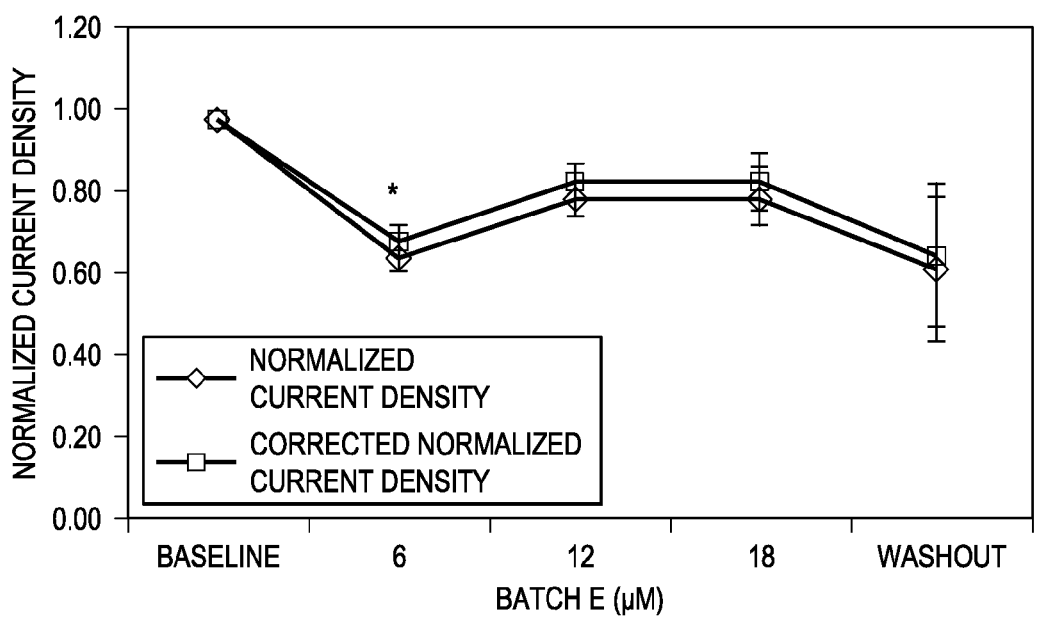
FIG. 24 shows effect of batch E on hERG current density from transfected HEK 293 cells at 20 mV.
FIG. 25 shows the effect of batch E on hERG current density from transfected HEK 293 cells at 20 mV.
Figures 26, 27:
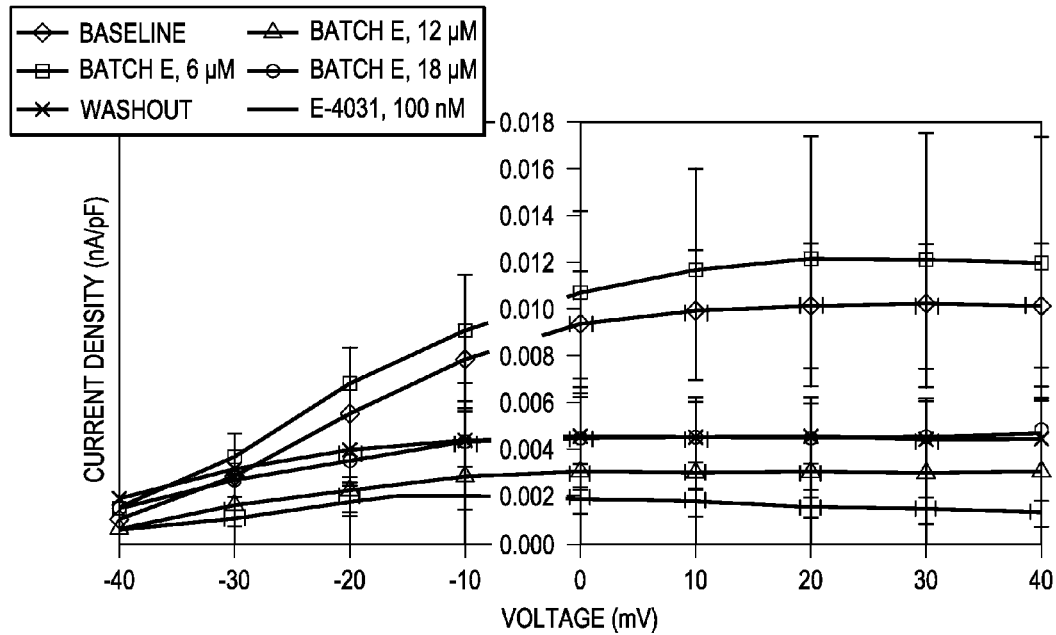
FIG. 26 shows relationship (I-V) of hERG current amplitude from transfected HEK 293 cells exposed to Batch E.
FIG. 27 shows the effect of tested compounds on hERG current density at +20 mV.

MTT Assay: This assay was carried out in pancreatic cancer cell line, MiaPaCa. The $IC_{50}$ for the HNC formulation was found to be at 22 μM concentration (FIG. 10). To determine the effect of hybrid nanoparticles on cell growth, cell viability (MTT) assay was carried out in pancreatic prostate and breast cancer cell lines. The inhibition in cell growth was measured by the MTT assay. For this assay, ~2000 cells/well were plated in a 96-well plate and were treated with different μM concentrations of free drug and equivalent doses of drug-loaded hybrid nanoparticles. The assay was terminated after 48 and 72 hours and relative growth inhibition compared to control cells was measured. All studies were set up in triplicates and repeated twice for statistical analysis. Results were expressed as mean±S.D.

Figure 9:
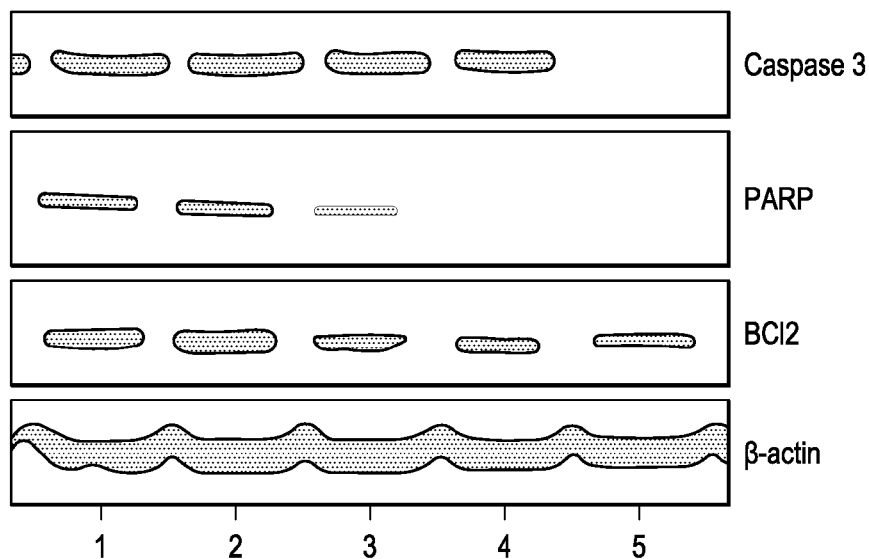
FIG. 9 shows Western blot analysis of MiaPaCa cells treated with hybrid nanocurcumin (25 μM (micromolar)). Lane 1: Untreated; lane 2: Blank nanoparticle; lane 3: Curcumin (24 hrs); lane 4: HNC (24 hrs) and; lane 5 HNC (48 hrs).

Results of western blot analysis of MiaPaCa cells treated with hybrid nanocurcumin (25 μM (micromolar)); untreated; blank nanoparticle; Curcumin (24 hrs); HNC (24 hrs) and; HNC (48 hrs) are provided in FIG. 9.

Example II

Evaluation of the effects of Liposoma-PLGA curcumin on the human potassium channel using human embryonic kidney (HEK) 293 cells transfected with a human ether-a-gogo-related gene (hERG): The example deals with quantifying the in vitro effects of Liposoma-PLGA curcumin on the potassium-selective IKr current generated in normoxic conditions in stably transfected HEK 293 cells. The hERG assay is used to assess the potential of a compound to interfere with the rapidly activating delayed-rectifier potassium channel; and is based on current International Conference on Harmonisation (ICH) Harmonized Tripartite Guidelines [ICH S7a/b] and generally accepted procedures for the testing of pharmaceutical compounds.

Study outline: Test articles: Batch A, Batch B, Batch C, Batch D and Batch E. Test System: hERG-expressing HEK 293 transfected cell line. Test performed: Whole-cell patch-clamp current acquisition and analysis. Study Temperature: 35+/−2° C.

Application of test articles, positive control and vehicle: 5 minutes of exposure to each concentration in presence of closed circuit perfusion (2 mL/min). 5 minutes for washout period in presence of a flow-through perfusion (2 mL/min) in addition to a closed circuit perfusion (2 mL/min). The positive control (100 nM E-4031) was added to naive cells obtained from the same cell line and same passage for a period of 5 minutes in presence of a closed circuit perfusion (2 mL/min).

Cells were under continuous stimulation of the pulses protocol throughout the studies and cell currents were recorded after 5 minutes of exposure to each condition.

Original data acquisition design is shown in FIG. 11.

Design for acquisition when testing the test articles or vehicle:
1 recording made in baseline condition
1 recording made in the presence of concentration 1, 2 or 3
1 recording made after washout (only after the concentration 3)

Design for acquisition when testing the positive control:
1 recording made in baseline condition
1 recording made in the presence of the positive control
n=number of responsive cells patched on which the whole protocol above could be applied Statistical analysis: Statistical comparisons were made using paired Student's t-tests. For the test articles, the currents recorded after exposure to the different test article concentrations were statistically compared to the currents recorded in baseline conditions. Currents recorded after the washout were statistically compared to the currents measured after the highest concentration of test articles. In the same way, currents recorded after the positive control were compared to the currents recorded in baseline conditions.

Differences were considered significant when $p<0.05$.
Exclusion criteria:
1. Timeframe of drug exposure not respected
2. Instability of the seal
3. No tail current generated by the patched cell
4. No significant effect of the positive control
5. More than 10% variability in capacitance transient amplitude over the duration of the study.

Effect of the Test Articles on Whole-Cell IKr hERG Currents:

Whole-cell currents elicited during a voltage pulse were recorded in baseline conditions and following the application of the selected concentrations of test articles. Currents were also recorded following a washout period. The cells were depolarized for one second from the holding potential (−80 mV) to a maximum value of +40 mV, starting at −40 mV and progressing in 10 mV increments. The membrane potential was then repolarized to −55 mV for one second, and finally returned to −80 mV.

Whole-cell tail current amplitude was measured at a holding potential of −55 mV, following activation of the current from −40 to +40 mV. Current amplitude was measured at the maximum (peak) of this tail current. Current density was obtained by dividing current amplitude by cell capacitance measured prior to capacitive transient minimization. As per protocol, 3 concentrations of each test article were analyzed for hERG current inhibition.

Figure 6:
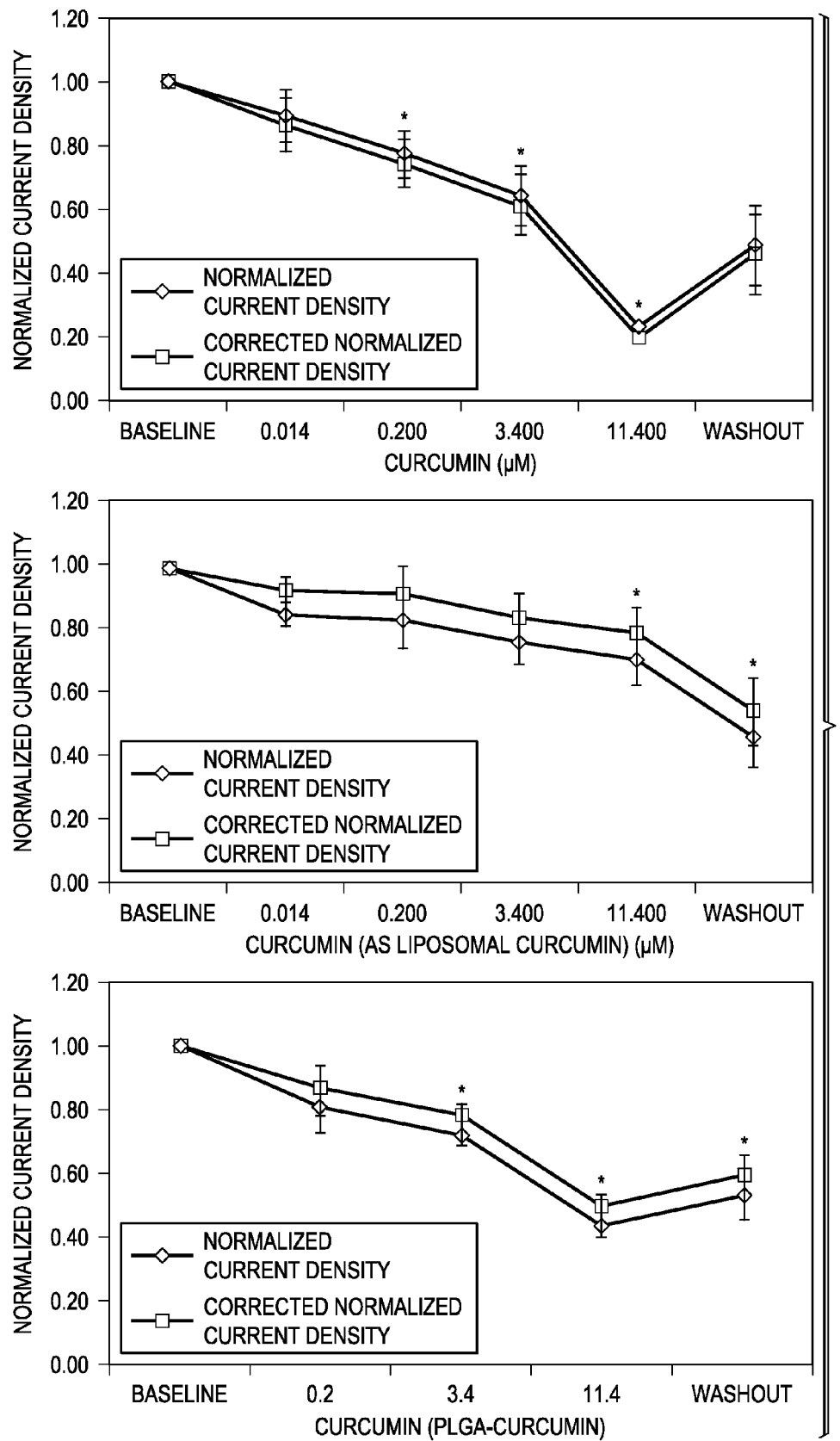
FIG. 6 shows hERG current density analysis of curcumin; liposomal curcumin; and PLGA curcumin.
Figure 7:
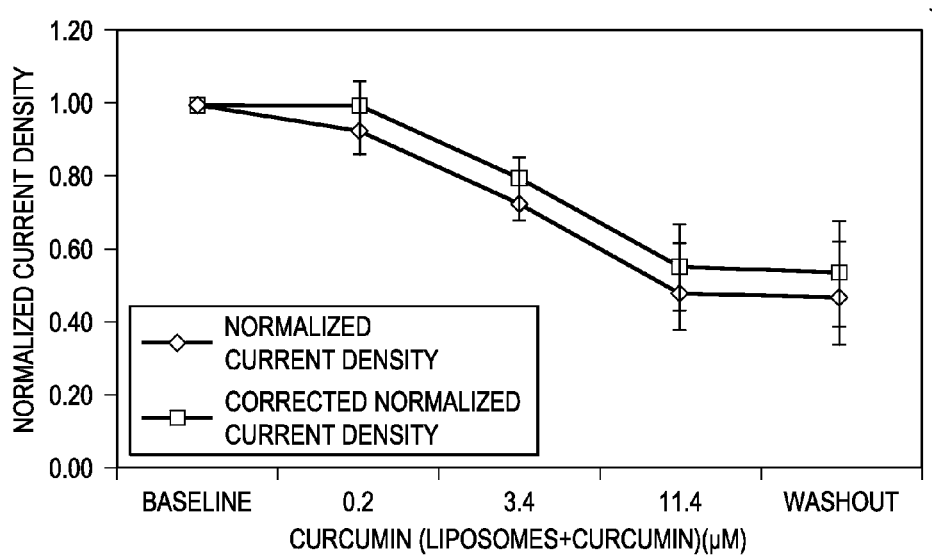
FIG. 7 shows hERG current density analysis of liposomes+ curcumin; and liposomes.
Figure 7:
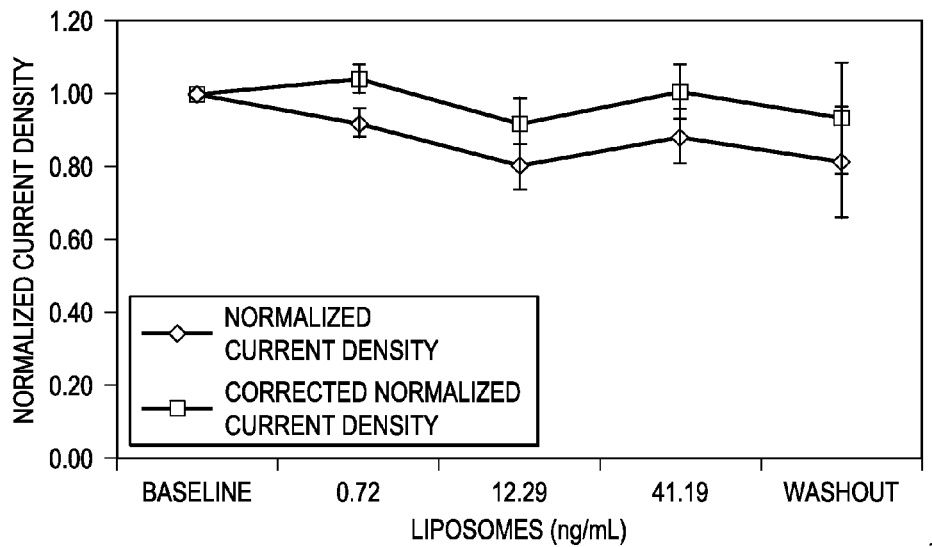

Result of the studies showing hERG current density analysis of curcumin; liposomal curcumin; and PLGA curcumin are provided in FIGS. 6 and 7, which show hERG current density analysis of liposomes+curcumin; and liposomes.

Current run-down and solvent effect correction. All data points presented in this Results Report have been corrected for solvent effect and time-dependent current run-down. Current run-down and solvent effects were measured simultaneously by applying the study design in test-article free conditions (hERG external solution or DMSO) over the same time frame as was done with the test articles. The loss in current amplitude measured during these so-called vehicle studies (representing both solvent effects and time-dependent run-down) was subtracted from the loss of amplitude measured in the presence of the test articles to isolate the effect of the test articles, apart from the effect of the solvent and the inevitable run-down in current amplitude over time.

This results, as shown in FIG. 11-27, quantify the effect of Liposomal-PLGA curcumin (Batch A, Batch B, Batch C, Batch D and Batch E) on the rapidly activating delayed-rectifier potassium selective current (IKr) generated under normoxic conditions in stably transfected Human Embryonic Kidney (HEK) 293 cells.

The concentrations of curcumin (6, 12 and 18 μM) were selected and reflect a range estimated to exceed the therapeutic.

To confirm the reversal effect of the test articles, cells exposed to the highest concentration (18 μM) were subject to a washout period of 5 minutes. The current measured after the washout period was not statistically different when compared to the current left after highest concentration exposure of the compounds showing that the effect of these compounds was not reversible.

E-4031 is one of the most selective hERG inhibitors available to date. It was selected to demonstrate the sensitivity of the test system. Three naive HEK293-hERG cells were exposed to 100 nM E-4031. E-4031 induced a significant inhibition of 81.8% of the current amplitude for I+20.

Sample Information: Store at −20° C., and protected from direct sunlight:
1) Batch A—
   Total weight of sample—215 mg
   Curcumin content—18 micro g/mg of test sample
   Material used—Polymer (PLGA), Lipid (DMPC+DMPG), Curcumin, sucrose.
2) Batch B—
   Total weight of sample—200 mg
   Curcumin content—6.8 micro g/mg of test sample
   Material used—Polymer (PLGA), Lipid (DMPC+DMPG), Curcumin, sucrose.
3) Batch C—
   Total weight of sample—200 mg
   Curcumin content—18.2 micro g/mg of test sample
      Material used—Polymer (PLGA), Chitosan, Polyvinyl alcohol (PVA), Lipid (DMPC+DMPG), Curcumin, sucrose.
4) Batch D—Pure curcumin
   Total weight—50 mg.
   5) Batch E—Liposomal curcumin
   Total volume—5 ml
   Curcumin content—6.4 mg/ml
   Material used—Lipid (DMPC+DMPG), Curcumin
   Molecular weight information:
   Curcumin Molecular weight—368.38 g/mol
   PLGA (50:50)—Molecular weight—124 kDa
   DMPC (PC (14:0/14:0))—Molecular weight—677.933 g/mol
   DMPG—Molecular weight—688.845 g/mol
   Sucrose—Molecular Weight 342.30 g/mol
   Chitosan—Low Molecular weight—75-85% deacetylated
   Polyvinyl alcohol (PVA)—Average molecular weight—30,000-70,000.

It is contemplated that any embodiment discussed in this specification can be implemented with respect to any method, kit, reagent, or composition of the invention, and vice versa. Furthermore, compositions of the invention can be used to achieve methods of the invention.

Evaluation of the Effects of Curcumin ER and Liposomal Curcumin on H-460 and A-549 Lung Cancer Mouse Xenograft Model.

The purpose of this study was to quantify the mean tumor volume of the mouse xenograft model over duration of the treatment. Specifically, the encapsulated and liposomally coated Curcumin ER and Liposomal Curcumin were tested using the cell lines H-460 and A-549, lung cancer xenograft model. Briefly, Female Hsd:athymic Nude-Foxn1nu mice 3-4 weeks old were obtained from Harlan Laboratories, USA. The cancer cells were injected into the mice and tumor volume was evaluated. The liposomal curcumins, Curcumin ER and Liposomal Curcumin, were administered via subcutaneous injection at a dose of 20 mg/kg body weight once in a week.

Figure 28:
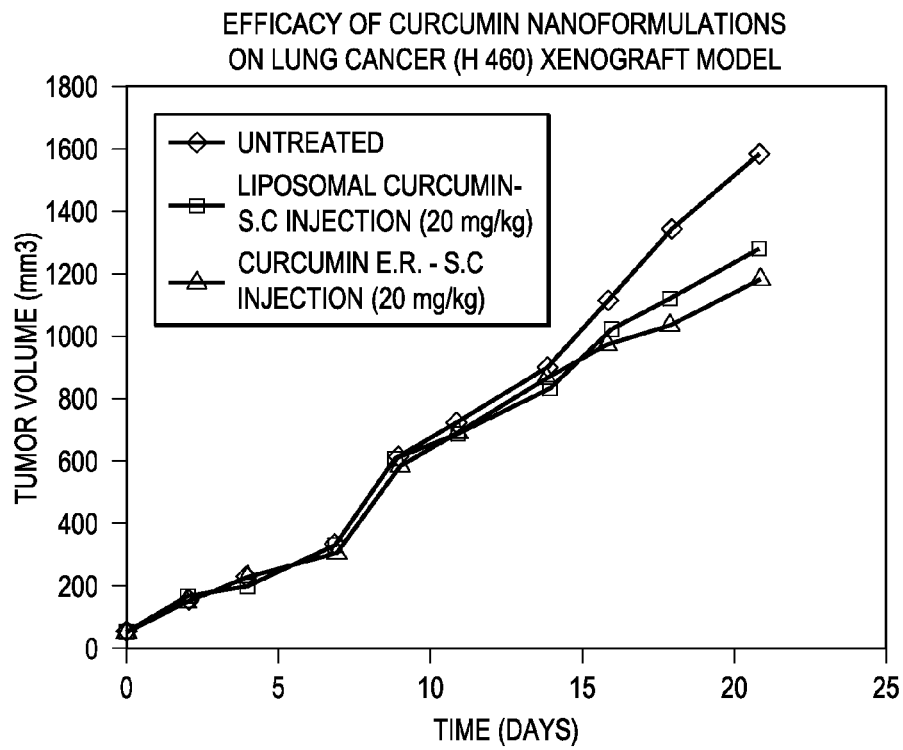
FIG. 28 shows the results of the treatment of breast cancer in a cancer xenograft mouse model system.
Figure 29:
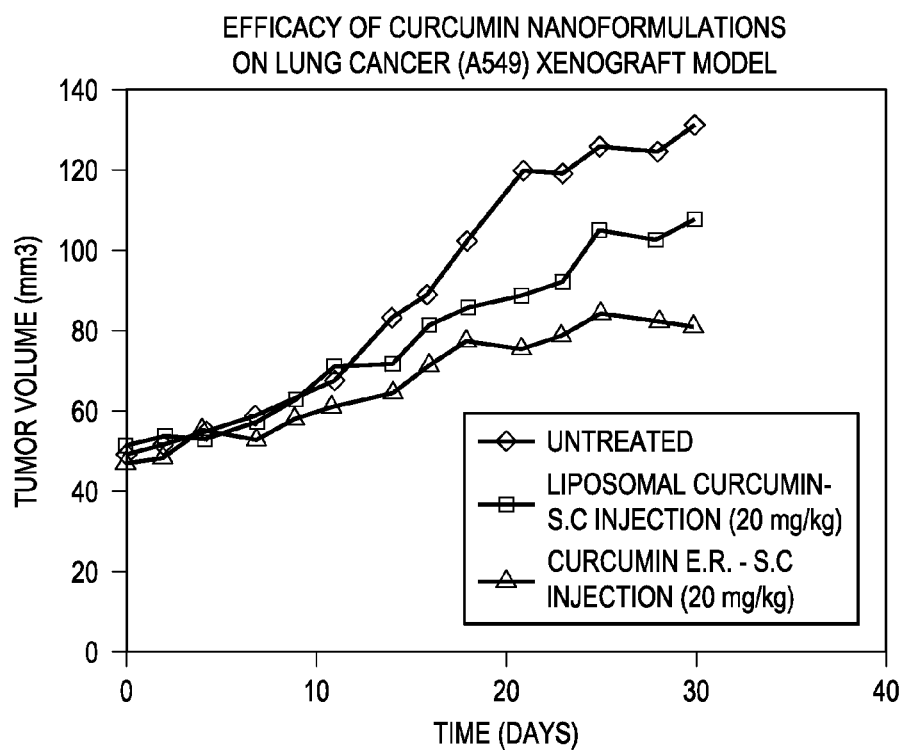
FIG. 29 shows additional results of the treatment of a different breast cancer in a cancer xenograft mouse model system.

FIG. 28 shows the results of the treatment of the H-460 breast cancer cell line in the Hsd:Athymic Nude-Foxn1nu mice. FIG. 29 shows additional results of the treatment of the A-549 breast cancer cell line in the Hsd:athymic Nude-Foxn1nu mice.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of forming a nanoparticle that does not cause QT prolongation when provided to a subject composition comprising:
   forming an organic phase by combining one or more polymers, one or more solvents and at least one of curcumin or curcuminoids;
   forming a lipid aqueous phase by mixing one or more lipids with water;
   mixing the organic phase with the lipid aqueous phase, whereby an emulsion is formed; and
   incubating the emulsion, whereby self-assembly of nanoparticles occurs and wherein the curcumin or curcuminoids nanoparticles does not cause QT prolongation when provided to a subject.

2. The method of claim 1, wherein the one or more polymers comprise at least one or poly(lactic-co-glycolic acid) (PLGA), poly(lactic acid), polylactide (PLA), and poly-L-lactide-co-ε-caprolactone (PLCL).

3. The method of claim 1, wherein the organic phase comprises PLGA in a concentration of 2-90 mg/ml.

4. The method of claim 1, wherein the organic phase comprises curcumin in a concentration of 1-15 weight % to volume.

5. The method of claim 1, wherein the one or more solvents comprises an organic solvent selected from at least one or acetonitrile, acetone, tert butyl alcohol, dimethyl formamide, and hexafluro isopropanol.

6. The method of claim 1, wherein the one or more lipids comprise at least one or DMPC, DMPG, 1,2-dioctadecanoyl-sn-glycero-3-phosphoethanolamine (DSPE), 1,2-distearoyl-sn-glycero-3-phosphoethanolamine-N-[amino(polyethylene glycol)(DSPE-PEG), DMPE PEG Maleimide, Lecithin, cholesterol, 1,2-dimyristoyl-sn-glycero-3-phosphoethanolamine-N-(lissamine rhodamine B sulfonyl) (ammonium salt), and 1,2-dimyristoyl-sn-glycero-3-phosphoethanolamine-N-(7-nitro-2-1,3-benzoxadiazol-4-yl) (ammonium salt).

7. The method of claim 1, wherein the one or more lipids comprise DMPC and DMPG in a molar ratio of 9:1, 7:3, 8:2, or 7.5:2.5.

8. The method of claim 1, wherein mixing the organic phase with the lipid aqueous phase comprises at least one of stirring the organic phase into the lipid aqueous phase, mixing the organic phase with the lipid aqueous phase comprises vortexing, or mixing the organic phase with the lipid aqueous phase further comprises sonicating.

9. The method of claim 1, wherein incubating the emulsion comprises stirring the emulsion for 2 hours.

10. The method of claim 1, further comprising one or more of the following: (1) separating the nanoparticles after incubating the emulsion; (2) filtering the nanoparticles after incubating the emulsion; (3) freezing the nanoparticles; (4) lyophilizing the nanoparticles; or (5) attaching a targeting agent to the nanoparticles.

11. The method of claim 1, further comprising the attaching at least one targeting agent, wherein the targeting agent selectively targets the nanoparticle to diseased tissue/cells, thereby minimizing whole body dose.

12. The method of claim 1, further comprising attaching at least one targeting agent to the nanoparticles, wherein the targeting agent comprises an antibody or functional fragment thereof that is capable of recognizing a target antigen.

13. The method of claim 1, wherein the nanoparticles have a size of 90 to 150 nm.

14. A method of forming a nanoparticle that prevents the active agent from causing QT prolongation caused by curcumin or a curcuminoid comprising:
   forming an organic phase by combining one or more polymers, one or more solvents and the active agent that causes QT prolongation;
   forming a lipid aqueous phase by mixing one or more lipids with water;
   mixing the organic phase with the lipid aqueous phase, whereby an emulsion is formed; and
   incubating the emulsion, whereby self-assembly of nanoparticles occurs, wherein the nanoparticle does not cause QT prolongation when provided to a subject.

* * * * *